US012788700B2

(12) United States Patent
Cavaco Paulo et al.

(10) Patent No.: US 12,788,700 B2
(45) Date of Patent: Nov. 10, 2026

(54) HAIR CLEANSER COMPOSITION, METHODS AND USES THEREOF

(71) Applicant: K18, Inc., San Francisco, CA (US)

(72) Inventors: Artur Manuel Cavaco Paulo, Braga (PT); Karis Staley, Huntington Beach, CA (US); Meagan Schlapp, Maspeth, NY (US)

(73) Assignee: K18, INC., San Francisco, CA (US)

( * ) Notice: Subject to any disclaimer, the term of this patent is extended or adjusted under 35 U.S.C. 154(b) by 161 days.

(21) Appl. No.: 18/339,889

(22) Filed: Jun. 22, 2023

(65) Prior Publication Data

US 2023/0414478 A1 Dec. 28, 2023

Related U.S. Application Data

(60) Provisional application No. 63/354,514, filed on Jun. 22, 2022.

(51) Int. Cl.

| | |
|---|---|
| ***A61Q 5/02*** | (2006.01) |
| ***A61K 8/34*** | (2006.01) |
| ***A61K 8/362*** | (2006.01) |
| ***A61K 8/368*** | (2006.01) |
| ***A61K 8/44*** | (2006.01) |
| ***A61K 8/46*** | (2006.01) |
| ***A61K 8/64*** | (2006.01) |
| ***A61K 8/67*** | (2006.01) |
| ***A61Q 5/12*** | (2006.01) |

(52) U.S. Cl.

CPC ................ *A61K 8/64* (2013.01); *A61K 8/345* (2013.01); *A61K 8/362* (2013.01); *A61K 8/368* (2013.01); *A61K 8/442* (2013.01); *A61K 8/466* (2013.01); *A61K 8/673* (2013.01); *A61Q 5/02* (2013.01); *A61Q 5/12* (2013.01); *A61K 2800/596* (2013.01)

(58) Field of Classification Search

None

See application file for complete search history.

(56) References Cited

U.S. PATENT DOCUMENTS

| | | | |
|---|---|---|---|
| 5,028,419 | A | 7/1991 | Pigiet |
| 5,635,170 | A | 6/1997 | Lang et al. |
| 6,020,163 | A | 2/2000 | Conklin |
| 7,622,273 | B2 | 11/2009 | Gibbs |
| 7,919,456 | B2 | 4/2011 | Ghosh |
| 8,034,338 | B2 | 10/2011 | Loibner et al. |
| 8,383,580 | B2 | 2/2013 | Rui et al. |
| 8,809,259 | B2 | 8/2014 | Berry et al. |
| 9,713,604 | B2 | 7/2017 | Dreher |
| 10,709,655 | B2 | 7/2020 | Cavaco et al. |
| 11,642,298 | B2 | 5/2023 | Cavaco Paulo et al. |
| 12,102,706 | B2 | 10/2024 | Cavaco Paulo et al. |
| 12,115,242 | B2 | 10/2024 | Cavaco Paulo et al. |
| 12,329,841 | B2 | 6/2025 | Cavaco Paulo et al. |
| 12,357,556 | B2 | 7/2025 | Sahib et al. |
| 12,383,484 | B2 | 8/2025 | Cavaco Paulo et al. |
| 2006/0223728 | A1 | 10/2006 | Tokunaga |
| 2006/0272103 | A1 | 12/2006 | Barbarat |
| 2006/0286655 | A1 | 12/2006 | Philippe |
| 2008/0107614 | A1 | 5/2008 | Fahnestock et al. |
| 2009/0130154 | A1 | 5/2009 | Gupta |
| 2010/0015070 | A1 | 1/2010 | Bollschweiler et al. |
| 2010/0272666 | A1 | 10/2010 | Breakspear et al. |
| 2012/0087862 | A1 | 4/2012 | Hood et al. |
| 2013/0059772 | A1 | 3/2013 | Kumar |
| 2013/0224269 | A1 | 8/2013 | Khan et al. |
| 2016/0175209 | A1 | 6/2016 | Walker et al. |
| 2016/0271043 | A1* | 9/2016 | Cavaco Paulo ........ A61K 8/645 |
| 2017/0333323 | A1* | 11/2017 | D'Arras ................ A61K 8/466 |
| 2020/0069551 | A1 | 3/2020 | Sahib et al. |
| 2020/0121581 | A1 | 4/2020 | Shoseyov et al. |
| 2020/0170929 | A1* | 6/2020 | Do .......................... A61Q 5/02 |
| 2021/0393500 | A1 | 12/2021 | Cavaco Paulo et al. |
| 2022/0151977 | A1 | 5/2022 | Stamps et al. |
| 2022/0287944 | A1 | 9/2022 | Costache et al. |
| 2023/0248627 | A1 | 8/2023 | Cavaco Paulo et al. |

(Continued)

FOREIGN PATENT DOCUMENTS

| | | | | |
|---|---|---|---|---|
| CA | 2309413 | A1 * | 11/2000 | ............. A61K 8/731 |
| CN | 103126949 | A | 6/2013 | |

(Continued)

OTHER PUBLICATIONS

What is wrong with CANTU shampoo. https://forums.longhaircommunity.com/showthread.php?t=149761. Published: May 5, 2019.*

Solu Shampoo. https://web.archive.org/web/20200929001233/https://www.thekindestcut.com/product-page/solu-shampoo. Published: Sep. 29, 2020.*

(Continued)

*Primary Examiner* — David J Blanchard

*Assistant Examiner* — Lori K Mattison

(74) *Attorney, Agent, or Firm* — WILSON SONSINI GOODRICH & ROSATI

(57) ABSTRACT

The present disclosure provides a hair cleanser composition for cleansing and repairing hair. The hair cleanser compositions described herein have a pH optimized to cleanse the hair and scalp. The pH of the hair cleanser composition minimizes reduces swelling and protein loss. The hair cleanser compositions described herein comprise peptides, which are based on the structure of keratin and keratin associated proteins. The peptides described bind hair with high affinity and repair keratinous fiber damage through the formation of disulfide bonds and other bonding interactions such as hydrogen bonds, ionic bonds, and Van der Waals interactions.

14 Claims, No Drawings

Specification includes a Sequence Listing.

(56) References Cited

U.S. PATENT DOCUMENTS

| | | | |
|---|---|---|---|
| 2023/0248631 A1 | 8/2023 | Cavaco Paulo et al. | |
| 2023/0301894 A1 | 9/2023 | Cavaco Paulo et al. | |
| 2023/0338263 A1 | 10/2023 | Cavaco Paulo et al. | |
| 2023/0355499 A1 | 11/2023 | Sahib et al. | |
| 2023/0414479 A1 | 12/2023 | Cavaco et al. | |
| 2023/0415070 A1 | 12/2023 | Cavaco et al. | |
| 2024/0082135 A1 | 3/2024 | Cavaco Paulo et al. | |
| 2024/0108560 A1 | 4/2024 | Staley et al. | |
| 2024/0115481 A1 | 4/2024 | Cavaco Paulo et al. | |
| 2024/0316187 A1 | 9/2024 | Von Mutius et al. | |

FOREIGN PATENT DOCUMENTS

| | | | | |
|---|---|---|---|---|
| CN | 104940071 A | 9/2015 | | |
| EP | 0335654 A2 | 10/1989 | | |
| EP | 0488242 A1 | 6/1992 | | |
| EP | 1046390 A1 * | 10/2000 | ............... A61K 8/24 | |
| EP | 1238645 A2 | 9/2002 | | |
| EP | 1705188 A1 | 9/2006 | | |
| FR | 2706300 A1 | 12/1994 | | |
| FR | 2876286 A1 | 4/2006 | | |
| GB | 103484 A | 1/1918 | | |
| JP | H0656889 A | 3/1994 | | |
| JP | H1112138 A | 1/1999 | | |
| JP | 2005151849 A | 6/2005 | | |
| KR | 20090070272 A | 7/2009 | | |
| PT | 103484 A | 11/2007 | | |
| WO | WO-9711672 A1 | 4/1997 | | |
| WO | WO-0023039 A2 | 4/2000 | | |
| WO | WO-0051556 A1 | 9/2000 | | |
| WO | WO-0064405 A2 | 11/2000 | | |
| WO | WO-0112806 A2 | 2/2001 | | |
| WO | WO-0123890 A1 | 4/2001 | | |
| WO | WO-2004048399 A2 | 6/2004 | | |
| WO | WO-2005049834 A1 | 6/2005 | | |
| WO | WO-2006001536 A1 | 1/2006 | | |
| WO | WO-2007136286 A1 | 11/2007 | | |
| WO | WO-2008081348 A2 | 7/2008 | | |
| WO | WO-2010010145 A1 | 1/2010 | | |
| WO | WO-2010089228 A1 | 8/2010 | | |
| WO | WO-2011072991 A1 | 6/2011 | | |
| WO | WO-2012013593 A1 | 2/2012 | | |
| WO | WO-2015056216 A2 | 4/2015 | | |
| WO | WO-2018095813 A1 * | 5/2018 | ............... A61K 8/20 | |
| WO | WO-2020031150 A1 | 2/2020 | | |
| WO | WO-2020181395 A1 | 9/2020 | | |
| WO | WO-2021001289 A1 | 1/2021 | | |
| WO | WO-2021260667 A2 | 12/2021 | | |
| WO | WO-2022003655 A1 | 1/2022 | | |
| WO | WO-2022029147 A1 | 2/2022 | | |
| WO | WO-2022072696 A1 | 4/2022 | | |
| WO | WO-2022101490 A1 | 5/2022 | | |
| WO | WO-2023081711 A1 | 5/2023 | | |
| WO | WO-2023161711 A1 | 8/2023 | | |
| WO | WO-2023250104 A2 | 12/2023 | | |
| WO | WO-2023250105 A1 | 12/2023 | | |
| WO | WO-2024073683 A2 | 4/2024 | | |
| WO | WO-2024147108 A1 | 7/2024 | | |
| WO | WO-2024166050 A1 | 8/2024 | | |
| WO | WO-2024206473 A1 | 10/2024 | | |
| WO | WO-2025137392 A1 | 6/2025 | | |
| WO | WO-2025137404 A1 | 6/2025 | | |

OTHER PUBLICATIONS

Chemists Corner. https://chemistscorner.com/cosmeticsciencetalk/discussion/sodium-pca-vs-glycerin/. Published: Dec. 1, 2020.*

Disodium 2-sulfolaurate. https://lerochem.eu/en/pagrindinis/347-disodium-2-sulfolaurate-d2s-90-kg.html?srsltid=AfmBOoplke4INGaiLr56tjtHo0wM06Yh59ennCUxBnEZ657Cd-G9FVfV. Published: 2019.*

Panthenol. https://web.archive.org/web/20200605044853/https://www.humblebeeandme.com/project/panthenol-vitamin-b5/. Published: Jun. 5, 2020.*

Blast glossary downloaded from www.ncbi.nlm.nih.gov on May 2, 2020.

Blast search for SEQ ID No. 1, downloaded May 2, 2020 (2020).

BLAST search for SEQ ID No. 2, downloaded May 2, 2020 (2020).

Co-pending U.S. Appl. No. 18/164,515, inventors Sahib; Suveen [Us] et al., filed Feb. 3, 2023.

Co-pending U.S. Appl. No. 18/194,372, inventors Cavaco Paulo; Arthur Manuel et al., filed Mar. 31, 2023.

Co-pending U.S. Appl. No. 18/334,287, inventors Cavaco Paulo; Arthur Manuel et al., filed Jun. 13, 2023.

Co-pending U.S. Appl. No. 18/339,927, inventors Cavaco; Paulo Artur Manuel et al., filed Jun. 22, 2023.

Dow, Carbowax Sentry Polyethylene Glycols, published online 2011.

Fernanda Reis Gavazzoni Dias. Hair Cosmetics: An Overview. International Journal of Trichology 7:2-15 (2015).

Fernandes et al. Keratin-based peptide: biological evaluation and strengthening properties on relaxed hair. International Journal of Cosmetic Science 34(4):338-346 (2012).

Koonin et al. Chapter 2 Evolutionary Concept in Genetics and Genomics. MY. Sequence—Evolution—Function: Computational Approaches in Comparative Genomics. Boston: Kluwer Academic. Available from: https:// www.ncbi.nlnn.nih.gov/books/NBK20260/ (pp. 3 ) (2003).

Marabotti et al. The misuse of terms in scientific literature. Bioinformatics 26(19):2498 (2010).

Naturally Curly, http://www.naturallycurly.com/curlreading/kinky-hair-type-4a/ingredients-commonly-used-in-hair-care-productspeg-modified-materials/, published online Jun. 8, 2010.

PCT/IB2014/065375 International Search Report and Written Opinion dated Jun. 7, 2015.

Romanowski. An introduction to cosmetic technology. American Oil Chemists' Society. Available at https://www.aocs.org/stay-informed/inform-magazine/featured-articles/an-introduction-to-cosmetic-technology-april-2015?SSO=True (8 pgs.) (2015).

Shimomura et al. Human Hair Keratin-Associated Proteins. J Investig Dermatol Symp Proc 10:230-233 (2005).

Thesis from Celia Freitas Da Cruz, Unraveling and modulating human hair morphology features (192 pgs) (2012).

Uniprot Protein Database, protein accession A8MUX0 , Keratin-associated protein 16-1, accessed on Dec. 18, 2019.

Uniprot Protein Database, protein accession P26371 , Keratin-associated protein 5-9, accessed on Dec. 18, 2019.

Uniprot Protein Database, protein accession Q9NSB0, Type II hair keratin 6, accessed on Dec. 18, 2019.

Uniprot Protein Database, protein Accession Q9NSB5, accessed on Nov. 8, 2019.

Uniprot protein database, protein Type II hair keratin 1, protein accession Q9NSB5, accessed on Aug. 28, 2017.

U.S. Forest Service entry on soaps at www.fs.fed.us/wildflowers/ethnobotany/soaps.shtra, downloaded Sep. 29, 2020 (2020).

U.S. Appl. No. 15/030,313 Office Action dated Aug. 29, 2018.

U.S. Appl. No. 15/030,313 Office Action dated Aug. 31, 2017.

U.S. Appl. No. 15/030,313 Office Action dated Jan. 11, 2019.

U.S. Appl. No. 15/030,313 Office Action dated Jan. 24, 2018.

U.S. Appl. No. 15/030,313 Office Action dated Jul. 18, 2019.

U.S. Appl. No. 15/030,313 Office Action dated Mar. 2, 2017.

U.S. Appl. No. 16/122,796 Office Action dated Apr. 15, 2021.

U.S. Appl. No. 16/122,796 Office Action dated Apr. 28, 2023.

U.S. Appl. No. 16/122,796 Office Action dated Jan. 5, 2023.

U.S. Appl. No. 16/122,796 Office Action dated May 4, 2020.

U.S. Appl. No. 16/122,796 Office Action dated Oct. 1, 2020.

U.S. Appl. No. 16/122,796 Office Action dated Sep. 20, 2022.

U.S. Appl. No. 16/439,889 Office Action dated Apr. 1, 2022.

U.S. Appl. No. 16/439,889 Office Action dated Jan. 3, 2020.

U.S. Appl. No. 16/439,889 Office Action dated Sep. 15, 2022.

Yang. Chapter 36: Hair Care Cosmetics. Cosmetic Science and Technology: Theoretical Principles and Applications (pp. 601-615) (2017).

Co-pending U.S. Appl. No. 18/252,712, inventors Cavaco; Paulo Artur Manuel et al., filed May 11, 2023.

Co-pending U.S. Appl. No. 18/478,320, inventors Staley; Karis et al., filed Sep. 29, 2023.

(56) References Cited

OTHER PUBLICATIONS

Co-pending U.S. Appl. No. 18/497,900, inventors Cavaco Paulo; Arthur Manuel et al., filed Oct. 30, 2023.
Co-pending U.S. Appl. No. 18/520,428, inventors Cavaco Paulo; Artur Manuel et al., filed Nov. 27, 2023.
U.S. Appl. No. 18/164,515 Office Action dated Oct. 12, 2023.
U.S. Appl. No. 18/334,287 Office Action dated Oct. 10, 2023.
PCT/US2023/026017 International Search Report and Written Opinion dated Dec. 13, 2023.
PCT/US2023/026019 International Search Report and Written Opinion dated Dec. 5, 2023.
U.S. Appl. No. 18/194,372 Office Action dated Dec. 14, 2023.
U.S. Appl. No. 18/334,287 Office Action dated Feb. 6, 2024.
U.S. Appl. No. 18/339,889 Office Action dated Dec. 19, 2023.
U.S. Appl. No. 18/339,927 Office Action dated Jan. 24, 2024.
U.S. Appl. No. 18/497,900 Office Action dated Mar. 11, 2024.
Altschul, Stephen F. et al. Basic Local Alignment Search Tool. Journal of Molecular Biology 215(3):403-410 (1990).
Archunan. Odorant Binding Proteins: a key player in the sense of smell. Bioinformation 14(1):36-37 (2018).
Berendsen, HJ., A glimpse of the Holy Grail? Science 282(5389):642-643 (1998).
Bignetti et al. Purification and characterisation of an odorant-binding protein from cow nasal tissue. Eur. J. Biochem. 149:227-231 (1985).
Bignetti et al. The pyrazine-binding protein and olfaction. Comp. Biochem. Physiol., 90(1): 1-5 (1988).
Bradley et al. Limits of cooperativity in a structurally modular protein: response of the Notch ankyrin domain to analogous alanine substitutions in each repeat. J Mol Biol. 324(2):373-386 (2002).
Breer. Olfactory receptors: molecular basis for recognition and discrimination of odors. Anal Bioanal Chem 377(3):427-33 (2003).
Briand et al. Evidence of an Odorant-Binding Protein in the Human Olfactory Mucus: Location, Structural Characterization, and Odorant-Binding Properties. Biochemistry 41:7241-7252 (2002).
Campanella et al., MatGAT: An application that generates similarity/identity matrices using protein or DNA sequences. BMC Bioinformatics 4:29 (2003).
Capo et al. The porcine odorant-binding protein as molecular probe for benzene detection. PloS One 13(9):e0202630 (2018).
Castro et al. The Structural Properties of Odorants Modulate Their Association to Human Odorant Binding Protein. Biomolecules 11(2):145 (2021).
Cave et al. Progress in the development of olfactory-based bioelectronic chemosensors. Biosens Bioelectron 123:211-222 (2019).
Cennamo et al. Easy to Use Plastic Optical Fiber-Based Biosensor for Detection of Butanal. PloS One 10(3):e0116770 (2015).
CN104940071A English Translation Published: Sep. 30, 2015.
Dal Monte et al. Purification and characterization of two odorant-binding proteins from nasal tisue of rabbit and pig. Comp Biochem Physiol 99(2):445-451 (1991).
Di Pietrantonio et al. Detection of odorant molecules via surface acoustic wave biosensor array based on odorant-binding proteins. Biosens Bioelectron 41:328-34 (2013).
EP1238645A2 English Translation Published: Sep. 11, 2002.
Flower. Beyond the superfamily: the lipocalin receptors. Biochim Biophys Acta 1482:327-336 (2000).
Flower. The lipocalin protein family : structure and function. Biochem. J. 318(Pt 1)(Pt 1):1-14 (1996).
Garibotti et al. Three Odorant-binding Proteins from Rabbit Nasal Mucosa. Chem Senses 22(4):383-390 (1997).
Goncalves et al. OBP fused with cell-penetrating peptides promotes liposomal transduction. Colloids Surf B Biointerfaces 161:645-653 (2018).
Goncalves et al. Release of Fragrances from Cotton Functionalized with Carbohydrate-Binding Module Proteins. ACS Applied Mater Interfaces 11(31):28499-28506 (2019).
Goncalves et al. Two Engineered OBPs with opposite temperature-dependent affinities towards 1-aminoanthracene. Sci Rep 8 (1):14844 (2018).
Gongalves et al. 1-Aminoanthracene Transduction into Liposomes Driven by Odorant-Binding Protein Proximity. ACS Applied Mater Interfaces 10(32):27531-27539 (2018).
Han et al. Operating Mechanism and Molecular Dynamics of Pheromone-Binding Protein ASP1 as Influenced by pH. PLoS One 9(10):e110565 (2014).
Kozlowski. IPC—Isoelectric Point Calculator. Biol Direct 11(1):55 (2016).
Lazar et al. Molecular and Functional Characterization of an Odorant Binding Protein of the Asian Elephant, Elephas maximus: Implications for the Role of Lipocalins in Mammalian Olfaction. Biochemistry 41:11786-11794 (2002).
Lobel et al. Odorant of different chemical classes interact with distinct odorant binding protein subtypes. Chem Senses 27:39-44 (2002).
Malpeli et al. Chapter 9: Purification and Fluorescent Titration of Cellular Retinol-Binding Protein. In Methods in Molecular Biology; Redfern, C. P. F., Ed.; pp. 111-122 (1998).
Mazzini et al. Dissociation and unfolding of bovine odorant binding protein at acidic pH. J Struct Biol 159(1):82-91 (2007).
Mulla et al. Capacitance-modulated transistor detects odorant binding protein chiral interactions. Nature Commun 6:6010 (2015).
Needleman, Saul B. and Christian wunsch D. A general method applicable to the search for similarities in the amino acid sequence of two proteins. Journal of Molecular Biology 48(3):444-453 (1970).
Ngo, Thomas, et al., Computational Complexity, Protein Structure Prediction, and the Levinthal Paradox. Birkhauser Boston 491-495 (1994).
Nogueira et al. Peptide anchor for folate-targeted liposomal delivery. Biomacromolecules 16(9):2904-2910 (2015).
Ozeki et al. A study of the suppression of body odour in elderly subjects by anti-fungal agents. Int J Cosmet Sci 38(3):312-8 (2016).
Paolini et al. Porcine odorant-binding protein: structural stability and ligand affinities measured by Fourier-transform infrared spectroscopy and fluorescence spectroscopy. Biochim Biophys Acta 1431:179-188 (1999).
Parisi et al. Unfolding and refolding of porcine odorant binding protein in guanidinium hydrochloride: equilibrium studies at neutral pH. Biochim Biophys Acta 652(2): 115-125 (2003).
PCT/IB2021/056011 International Search Report and Written Opinion dated Oct. 6, 2021.
Pelosi et al. Odorant-Binding Proteins as Sensing Elements for Odour Monitoring. Sensors (Basel) 18(10):3248 (2018).
Pelosi et al. Structure and biotechnological applications of odorant-binding proteins. Appl Microbiol Biotechnol 98(1):61-70 (2014).
Pelosi. Odorant-Binding Proteins: Structural Aspects. In Annals New York academy of sciences; Olfaction and Taste XII: an international symposium, pp. 281-293 (1998).
Perduca et al. Crystal Structure of a Truncated Form of Porcine Odorant-Binding Protein. Proteins 42:201-209 (2001).
Pes et al. Isolation of two odorant-binding proteins from mouse nasal tissue. Comp. Biochem. Physiol. 103 (4):1011-1017 (1992).
Pevsner et al. Odorant-binding protein: characterization of ligand binding. J Biol Chem 265(11):6118-6125 (1990).
Rudinger, J., Characteristics of the amino acids as components of a peptide hormone sequence. Peptide Hormones, J.A, Parsons , MA, BM, BCh, 1-7 (1976).
Sankaran et al. Biology and applications of olfactory sensing system: A review. Sensors and Actuators B: Chemical 171-172:1-17 (2012).
Schinzel, R, et al., The Phosphate Recognition Site of *Escherichia coli* Maltodextrin Phosphorylase. FEBS Letters 286(1-2):125-128 (1991).
Sigma, Designing Custom Peptides, pp. 1-2. (2004).
Silva et al. Odorant binding proteins: a biotechnological tool for odour control. Appl Microbiol Biotechnol 98(8):3629-3638 (2014).
Sorokowska et al. Does Personality Smell? Accuracy of Personality Assessments Based on Body Odour. European Journal of Personality 26(5):496-503 (2012).
Spinelli et al. The Structure of the Monomeric Porcine Odorant Binding Protein Sheds Light on the Domain Swapping Mechanism. Biochemistry 37:7913-7918 (1998).

(56) References Cited

OTHER PUBLICATIONS

Tegoni et al. Mammalian odorant binding proteins. Biochim Biophys Acta 1482:229-240 (2000).
U.S. Appl. No. 18/164,515 Office Action dated Feb. 15, 2024.
U.S. Appl. No. 18/164,515 Office Action dated Jun. 5, 2024.
U.S. Appl. No. 18/339,927 Office Action dated May 8, 2024.
U.S. Appl. No. 18/520,428 Office Action dated Mar. 25, 2024.
Vincent et al. Crystal structures of bovine odorant-binding protein in complex with odorant molecules. Eur J Biochem 271(19):3832-42 (2004).
Voet, Judith., Biochemistry, Second Edition, John Wiley & Sons, Inc., 235-241 (1995).
Whitson et al. Human Odorant Binding Protein 2a has Two Affinity States and is Capable of Binding Some Uremic Toxins. Biochem Anal Biochem 3:2 (2014).
Yampolsky, Lev, et al., The Exchangeability of Amino Acids in Proteins. Genetics 170(4):1459-1472 (2005).
PCT/US2024/021721 International Search Report and Written Opinion dated Jul. 11, 2024.
The PH of Hair—The Difficult Truth About Shampoo. Love Curly Hair, Jun. 23, 2021: [Retrieved on Nov. 19, 2024]. Available at URL:https://web.archive.org/web/20210623093539/https://www.lovecurlyhair.com/the-ph-of-hair-the-difficult-truth-about-shampoo// pp. 1-22.
U.S. Serial No. 18/003,127 Office Action dated Nov. 14, 2024.
U.S. Appl. No. 18/164,515 Office Action dated Sep. 16, 2024.
U.S. Appl. No. 18/339,927 Office Action dated Nov. 26, 2024.
U.S. Appl. No. 18/497,900 Office Action dated Jul. 17, 2024.
U.S. Appl. No. 18/520,428 Office Action dated Jul. 11, 2024.
Co-pending U.S. Appl. No. 19/242,603, inventors Sahib; Suveen et al., filed Jun. 18, 2025.
U.S. Serial No. 18/003, 127 Office Action dated May 12, 2025.
U.S. Appl. No. 18/339,927 Office Action dated May 6, 2025.

* cited by examiner

SEQUENCE LISTING

```
Sequence total quantity: 1131
SEQ ID NO: 1           moltype =   length =
SEQUENCE: 1
000

SEQ ID NO: 2           moltype =   length =
SEQUENCE: 2
000

SEQ ID NO: 3           moltype =   length =
SEQUENCE: 3
000

SEQ ID NO: 4           moltype =   length =
SEQUENCE: 4
000

SEQ ID NO: 5           moltype =   length =
SEQUENCE: 5
000

SEQ ID NO: 6           moltype =   length =
SEQUENCE: 6
000

SEQ ID NO: 7           moltype =   length =
SEQUENCE: 7
000

SEQ ID NO: 8           moltype =   length =
SEQUENCE: 8
000

SEQ ID NO: 9           moltype =   length =
SEQUENCE: 9
000

SEQ ID NO: 10          moltype =   length =
SEQUENCE: 10
000

SEQ ID NO: 11          moltype =   length =
SEQUENCE: 11
000

SEQ ID NO: 12          moltype =   length =
SEQUENCE: 12
000

SEQ ID NO: 13          moltype =   length =
SEQUENCE: 13
000

SEQ ID NO: 14          moltype =   length =
SEQUENCE: 14
000

SEQ ID NO: 15          moltype =   length =
SEQUENCE: 15
000

SEQ ID NO: 16          moltype =   length =
SEQUENCE: 16
000

SEQ ID NO: 17          moltype =   length =
SEQUENCE: 17
000
```

```
SEQ ID NO: 18          moltype =   length =
SEQUENCE: 18
000

SEQ ID NO: 19          moltype =   length =
SEQUENCE: 19
000

SEQ ID NO: 20          moltype =   length =
SEQUENCE: 20
000

SEQ ID NO: 21          moltype =   length =
SEQUENCE: 21
000

SEQ ID NO: 22          moltype =   length =
SEQUENCE: 22
000

SEQ ID NO: 23          moltype =   length =
SEQUENCE: 23
000

SEQ ID NO: 24          moltype =   length =
SEQUENCE: 24
000

SEQ ID NO: 25          moltype =   length =
SEQUENCE: 25
000

SEQ ID NO: 26          moltype =   length =
SEQUENCE: 26
000

SEQ ID NO: 27          moltype =   length =
SEQUENCE: 27
000

SEQ ID NO: 28          moltype =   length =
SEQUENCE: 28
000

SEQ ID NO: 29          moltype =   length =
SEQUENCE: 29
000

SEQ ID NO: 30          moltype =   length =
SEQUENCE: 30
000

SEQ ID NO: 31          moltype =   length =
SEQUENCE: 31
000

SEQ ID NO: 32          moltype =   length =
SEQUENCE: 32
000

SEQ ID NO: 33          moltype =   length =
SEQUENCE: 33
000

SEQ ID NO: 34          moltype =   length =
SEQUENCE: 34
000

SEQ ID NO: 35          moltype =   length =
SEQUENCE: 35
000

SEQ ID NO: 36          moltype =   length =
SEQUENCE: 36
000
```

```
SEQ ID NO: 37          moltype =   length =
SEQUENCE: 37
000

SEQ ID NO: 38          moltype =   length =
SEQUENCE: 38
000

SEQ ID NO: 39          moltype =   length =
SEQUENCE: 39
000

SEQ ID NO: 40          moltype =   length =
SEQUENCE: 40
000

SEQ ID NO: 41          moltype =   length =
SEQUENCE: 41
000

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype =   length =
SEQUENCE: 50
000

SEQ ID NO: 51          moltype =   length =
SEQUENCE: 51
000

SEQ ID NO: 52          moltype =   length =
SEQUENCE: 52
000

SEQ ID NO: 53          moltype =   length =
SEQUENCE: 53
000

SEQ ID NO: 54          moltype =   length =
SEQUENCE: 54
000

SEQ ID NO: 55          moltype =   length =
SEQUENCE: 55
000
```

SEQ ID NO: 56 moltype = length =
SEQUENCE: 56
000

SEQ ID NO: 57 moltype = length =
SEQUENCE: 57
000

SEQ ID NO: 58 moltype = length =
SEQUENCE: 58
000

SEQ ID NO: 59 moltype = length =
SEQUENCE: 59
000

SEQ ID NO: 60 moltype = length =
SEQUENCE: 60
000

SEQ ID NO: 61 moltype = length =
SEQUENCE: 61
000

SEQ ID NO: 62 moltype = length =
SEQUENCE: 62
000

SEQ ID NO: 63 moltype = length =
SEQUENCE: 63
000

SEQ ID NO: 64 moltype = length =
SEQUENCE: 64
000

SEQ ID NO: 65 moltype = length =
SEQUENCE: 65
000

SEQ ID NO: 66 moltype = length =
SEQUENCE: 66
000

SEQ ID NO: 67 moltype = length =
SEQUENCE: 67
000

SEQ ID NO: 68 moltype = length =
SEQUENCE: 68
000

SEQ ID NO: 69 moltype = length =
SEQUENCE: 69
000

SEQ ID NO: 70 moltype = length =
SEQUENCE: 70
000

SEQ ID NO: 71 moltype = length =
SEQUENCE: 71
000

SEQ ID NO: 72 moltype = length =
SEQUENCE: 72
000

SEQ ID NO: 73 moltype = length =
SEQUENCE: 73
000

SEQ ID NO: 74 moltype = length =
SEQUENCE: 74
000

```
SEQ ID NO: 75           moltype = AA  length = 10
FEATURE                 Location/Qualifiers
source                  1..10
                        mol_type = protein
                        organism = synthetic construct
SEQUENCE: 75
CLPCLPAASC                                                                 10

SEQ ID NO: 76           moltype =   length =
SEQUENCE: 76
000

SEQ ID NO: 77           moltype =   length =
SEQUENCE: 77
000

SEQ ID NO: 78           moltype =   length =
SEQUENCE: 78
000

SEQ ID NO: 79           moltype =   length =
SEQUENCE: 79
000

SEQ ID NO: 80           moltype =   length =
SEQUENCE: 80
000

SEQ ID NO: 81           moltype =   length =
SEQUENCE: 81
000

SEQ ID NO: 82           moltype =   length =
SEQUENCE: 82
000

SEQ ID NO: 83           moltype =   length =
SEQUENCE: 83
000

SEQ ID NO: 84           moltype =   length =
SEQUENCE: 84
000

SEQ ID NO: 85           moltype =   length =
SEQUENCE: 85
000

SEQ ID NO: 86           moltype =   length =
SEQUENCE: 86
000

SEQ ID NO: 87           moltype =   length =
SEQUENCE: 87
000

SEQ ID NO: 88           moltype =   length =
SEQUENCE: 88
000

SEQ ID NO: 89           moltype =   length =
SEQUENCE: 89
000

SEQ ID NO: 90           moltype =   length =
SEQUENCE: 90
000

SEQ ID NO: 91           moltype =   length =
SEQUENCE: 91
000
```

-continued

```
SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
000

SEQ ID NO: 95          moltype =   length =
SEQUENCE: 95
000

SEQ ID NO: 96          moltype =   length =
SEQUENCE: 96
000

SEQ ID NO: 97          moltype =   length =
SEQUENCE: 97
000

SEQ ID NO: 98          moltype =   length =
SEQUENCE: 98
000

SEQ ID NO: 99          moltype =   length =
SEQUENCE: 99
000

SEQ ID NO: 100         moltype =   length =
SEQUENCE: 100
000

SEQ ID NO: 101         moltype =   length =
SEQUENCE: 101
000

SEQ ID NO: 102         moltype =   length =
SEQUENCE: 102
000

SEQ ID NO: 103         moltype =   length =
SEQUENCE: 103
000

SEQ ID NO: 104         moltype =   length =
SEQUENCE: 104
000

SEQ ID NO: 105         moltype =   length =
SEQUENCE: 105
000

SEQ ID NO: 106         moltype =   length =
SEQUENCE: 106
000

SEQ ID NO: 107         moltype =   length =
SEQUENCE: 107
000

SEQ ID NO: 108         moltype =   length =
SEQUENCE: 108
000

SEQ ID NO: 109         moltype =   length =
SEQUENCE: 109
000

SEQ ID NO: 110         moltype =   length =
SEQUENCE: 110
000
```

```
SEQ ID NO: 111          moltype =   length =
SEQUENCE: 111
000

SEQ ID NO: 112          moltype =   length =
SEQUENCE: 112
000

SEQ ID NO: 113          moltype =   length =
SEQUENCE: 113
000

SEQ ID NO: 114          moltype =   length =
SEQUENCE: 114
000

SEQ ID NO: 115          moltype =   length =
SEQUENCE: 115
000

SEQ ID NO: 116          moltype =   length =
SEQUENCE: 116
000

SEQ ID NO: 117          moltype =   length =
SEQUENCE: 117
000

SEQ ID NO: 118          moltype =   length =
SEQUENCE: 118
000

SEQ ID NO: 119          moltype =   length =
SEQUENCE: 119
000

SEQ ID NO: 120          moltype =   length =
SEQUENCE: 120
000

SEQ ID NO: 121          moltype =   length =
SEQUENCE: 121
000

SEQ ID NO: 122          moltype =   length =
SEQUENCE: 122
000

SEQ ID NO: 123          moltype =   length =
SEQUENCE: 123
000

SEQ ID NO: 124          moltype =   length =
SEQUENCE: 124
000

SEQ ID NO: 125          moltype =   length =
SEQUENCE: 125
000

SEQ ID NO: 126          moltype =   length =
SEQUENCE: 126
000

SEQ ID NO: 127          moltype =   length =
SEQUENCE: 127
000

SEQ ID NO: 128          moltype =   length =
SEQUENCE: 128
000

SEQ ID NO: 129          moltype =   length =
SEQUENCE: 129
000
```

SEQ ID NO: 130 moltype = length =
SEQUENCE: 130
000

SEQ ID NO: 131 moltype = length =
SEQUENCE: 131
000

SEQ ID NO: 132 moltype = length =
SEQUENCE: 132
000

SEQ ID NO: 133 moltype = length =
SEQUENCE: 133
000

SEQ ID NO: 134 moltype = length =
SEQUENCE: 134
000

SEQ ID NO: 135 moltype = length =
SEQUENCE: 135
000

SEQ ID NO: 136 moltype = length =
SEQUENCE: 136
000

SEQ ID NO: 137 moltype = length =
SEQUENCE: 137
000

SEQ ID NO: 138 moltype = length =
SEQUENCE: 138
000

SEQ ID NO: 139 moltype = length =
SEQUENCE: 139
000

SEQ ID NO: 140 moltype = length =
SEQUENCE: 140
000

SEQ ID NO: 141 moltype = length =
SEQUENCE: 141
000

SEQ ID NO: 142 moltype = length =
SEQUENCE: 142
000

SEQ ID NO: 143 moltype = length =
SEQUENCE: 143
000

SEQ ID NO: 144 moltype = length =
SEQUENCE: 144
000

SEQ ID NO: 145 moltype = length =
SEQUENCE: 145
000

SEQ ID NO: 146 moltype = length =
SEQUENCE: 146
000

SEQ ID NO: 147 moltype = length =
SEQUENCE: 147
000

SEQ ID NO: 148 moltype = length =
SEQUENCE: 148
000

SEQ ID NO: 149 moltype = length =
SEQUENCE: 149
000

SEQ ID NO: 150 moltype = length =
SEQUENCE: 150
000

SEQ ID NO: 151 moltype = length =
SEQUENCE: 151
000

SEQ ID NO: 152 moltype = length =
SEQUENCE: 152
000

SEQ ID NO: 153 moltype = length =
SEQUENCE: 153
000

SEQ ID NO: 154 moltype = length =
SEQUENCE: 154
000

SEQ ID NO: 155 moltype = length =
SEQUENCE: 155
000

SEQ ID NO: 156 moltype = length =
SEQUENCE: 156
000

SEQ ID NO: 157 moltype = length =
SEQUENCE: 157
000

SEQ ID NO: 158 moltype = length =
SEQUENCE: 158
000

SEQ ID NO: 159 moltype = length =
SEQUENCE: 159
000

SEQ ID NO: 160 moltype = length =
SEQUENCE: 160
000

SEQ ID NO: 161 moltype = length =
SEQUENCE: 161
000

SEQ ID NO: 162 moltype = length =
SEQUENCE: 162
000

SEQ ID NO: 163 moltype = length =
SEQUENCE: 163
000

SEQ ID NO: 164 moltype = length =
SEQUENCE: 164
000

SEQ ID NO: 165 moltype = length =
SEQUENCE: 165
000

SEQ ID NO: 166 moltype = length =
SEQUENCE: 166
000

SEQ ID NO: 167 moltype = length =
SEQUENCE: 167
000

SEQ ID NO: 168 moltype = length =
SEQUENCE: 168
000

SEQ ID NO: 169 moltype = length =
SEQUENCE: 169
000

SEQ ID NO: 170 moltype = length =
SEQUENCE: 170
000

SEQ ID NO: 171 moltype = length =
SEQUENCE: 171
000

SEQ ID NO: 172 moltype = length =
SEQUENCE: 172
000

SEQ ID NO: 173 moltype = length =
SEQUENCE: 173
000

SEQ ID NO: 174 moltype = length =
SEQUENCE: 174
000

SEQ ID NO: 175 moltype = length =
SEQUENCE: 175
000

SEQ ID NO: 176 moltype = length =
SEQUENCE: 176
000

SEQ ID NO: 177 moltype = length =
SEQUENCE: 177
000

SEQ ID NO: 178 moltype = length =
SEQUENCE: 178
000

SEQ ID NO: 179 moltype = length =
SEQUENCE: 179
000

SEQ ID NO: 180 moltype = length =
SEQUENCE: 180
000

SEQ ID NO: 181 moltype = length =
SEQUENCE: 181
000

SEQ ID NO: 182 moltype = length =
SEQUENCE: 182
000

SEQ ID NO: 183 moltype = length =
SEQUENCE: 183
000

SEQ ID NO: 184 moltype = length =
SEQUENCE: 184
000

SEQ ID NO: 185 moltype = length =
SEQUENCE: 185
000

SEQ ID NO: 186 moltype = length =
SEQUENCE: 186
000

SEQ ID NO: 187 moltype = length =
SEQUENCE: 187
000

SEQ ID NO: 188 moltype = length =
SEQUENCE: 188
000

SEQ ID NO: 189 moltype = length =
SEQUENCE: 189
000

SEQ ID NO: 190 moltype = length =
SEQUENCE: 190
000

SEQ ID NO: 191 moltype = length =
SEQUENCE: 191
000

SEQ ID NO: 192 moltype = length =
SEQUENCE: 192
000

SEQ ID NO: 193 moltype = length =
SEQUENCE: 193
000

SEQ ID NO: 194 moltype = length =
SEQUENCE: 194
000

SEQ ID NO: 195 moltype = length =
SEQUENCE: 195
000

SEQ ID NO: 196 moltype = length =
SEQUENCE: 196
000

SEQ ID NO: 197 moltype = length =
SEQUENCE: 197
000

SEQ ID NO: 198 moltype = length =
SEQUENCE: 198
000

SEQ ID NO: 199 moltype = length =
SEQUENCE: 199
000

SEQ ID NO: 200 moltype = length =
SEQUENCE: 200
000

SEQ ID NO: 201 moltype = length =
SEQUENCE: 201
000

SEQ ID NO: 202 moltype = length =
SEQUENCE: 202
000

SEQ ID NO: 203 moltype = length =
SEQUENCE: 203
000

SEQ ID NO: 204 moltype = length =
SEQUENCE: 204
000

SEQ ID NO: 205 moltype = length =
SEQUENCE: 205
000

SEQ ID NO: 206 moltype = length =
SEQUENCE: 206
000

SEQ ID NO: 207 moltype = length =
SEQUENCE: 207
000

SEQ ID NO: 208 moltype = length =
SEQUENCE: 208
000

SEQ ID NO: 209 moltype = length =
SEQUENCE: 209
000

SEQ ID NO: 210 moltype = length =
SEQUENCE: 210
000

SEQ ID NO: 211 moltype = length =
SEQUENCE: 211
000

SEQ ID NO: 212 moltype = length =
SEQUENCE: 212
000

SEQ ID NO: 213 moltype = length =
SEQUENCE: 213
000

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223
000

SEQ ID NO: 224 moltype = length =
SEQUENCE: 224
000

SEQ ID NO: 225 moltype = length =
SEQUENCE: 225
000

SEQ ID NO: 226 moltype = length =
SEQUENCE: 226
000

SEQ ID NO: 227 moltype = length =
SEQUENCE: 227
000

SEQ ID NO: 228 moltype = length =
SEQUENCE: 228
000

SEQ ID NO: 229 moltype = length =
SEQUENCE: 229
000

SEQ ID NO: 230 moltype = length =
SEQUENCE: 230
000

SEQ ID NO: 231 moltype = length =
SEQUENCE: 231
000

SEQ ID NO: 232 moltype = length =
SEQUENCE: 232
000

SEQ ID NO: 233 moltype = length =
SEQUENCE: 233
000

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =
SEQUENCE: 243
000

SEQ ID NO: 244 moltype = length =
SEQUENCE: 244
000

SEQ ID NO: 245 moltype = length =
SEQUENCE: 245
000

SEQ ID NO: 246 moltype = length =
SEQUENCE: 246
000

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252
000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286
000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =
SEQUENCE: 306
000

SEQ ID NO: 307 moltype = length =
SEQUENCE: 307
000

SEQ ID NO: 308 moltype = length =
SEQUENCE: 308
000

SEQ ID NO: 309 moltype = length =
SEQUENCE: 309
000

SEQ ID NO: 310 moltype = length =
SEQUENCE: 310
000

SEQ ID NO: 311 moltype = length =
SEQUENCE: 311
000

SEQ ID NO: 312 moltype = length =
SEQUENCE: 312
000

SEQ ID NO: 313 moltype = length =
SEQUENCE: 313
000

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

-continued

SEQ ID NO: 320 moltype = length =
SEQUENCE: 320
000

SEQ ID NO: 321 moltype = length =
SEQUENCE: 321
000

SEQ ID NO: 322 moltype = length =
SEQUENCE: 322
000

SEQ ID NO: 323 moltype = length =
SEQUENCE: 323
000

SEQ ID NO: 324 moltype = length =
SEQUENCE: 324
000

SEQ ID NO: 325 moltype = length =
SEQUENCE: 325
000

SEQ ID NO: 326 moltype = length =
SEQUENCE: 326
000

SEQ ID NO: 327 moltype = length =
SEQUENCE: 327
000

SEQ ID NO: 328 moltype = length =
SEQUENCE: 328
000

SEQ ID NO: 329 moltype = length =
SEQUENCE: 329
000

SEQ ID NO: 330 moltype = length =
SEQUENCE: 330
000

SEQ ID NO: 331 moltype = length =
SEQUENCE: 331
000

SEQ ID NO: 332 moltype = length =
SEQUENCE: 332
000

SEQ ID NO: 333 moltype = length =
SEQUENCE: 333
000

SEQ ID NO: 334 moltype = length =
SEQUENCE: 334
000

SEQ ID NO: 335 moltype = length =
SEQUENCE: 335
000

SEQ ID NO: 336 moltype = length =
SEQUENCE: 336
000

SEQ ID NO: 337 moltype = length =
SEQUENCE: 337
000

SEQ ID NO: 338 moltype = length =
SEQUENCE: 338
000

SEQ ID NO: 339 moltype = length =
SEQUENCE: 339
000

SEQ ID NO: 340 moltype = length =
SEQUENCE: 340
000

SEQ ID NO: 341 moltype = length =
SEQUENCE: 341
000

SEQ ID NO: 342 moltype = length =
SEQUENCE: 342
000

SEQ ID NO: 343 moltype = length =
SEQUENCE: 343
000

SEQ ID NO: 344 moltype = length =
SEQUENCE: 344
000

SEQ ID NO: 345 moltype = length =
SEQUENCE: 345
000

SEQ ID NO: 346 moltype = length =
SEQUENCE: 346
000

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =
SEQUENCE: 351
000

SEQ ID NO: 352 moltype = length =
SEQUENCE: 352
000

SEQ ID NO: 353 moltype = length =
SEQUENCE: 353
000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

SEQ ID NO: 372 moltype = length =
SEQUENCE: 372
000

SEQ ID NO: 373 moltype = length =
SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =
SEQUENCE: 385
000

SEQ ID NO: 386 moltype = length =
SEQUENCE: 386
000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

SEQ ID NO: 392 moltype = length =
SEQUENCE: 392
000

SEQ ID NO: 393 moltype = length =
SEQUENCE: 393
000

SEQ ID NO: 394 moltype = length =
SEQUENCE: 394
000

SEQ ID NO: 395 moltype = length =
SEQUENCE: 395
000

```
SEQ ID NO: 396          moltype =   length =
SEQUENCE: 396
000

SEQ ID NO: 397          moltype =   length =
SEQUENCE: 397
000

SEQ ID NO: 398          moltype =   length =
SEQUENCE: 398
000

SEQ ID NO: 399          moltype =   length =
SEQUENCE: 399
000

SEQ ID NO: 400          moltype = AA  length = 13
FEATURE                 Location/Qualifiers
source                  1..13
                        mol_type = protein
                        organism = synthetic construct
SEQUENCE: 400
GGVCGPSPPC ITT                                                        13

SEQ ID NO: 401          moltype = AA  length = 11
FEATURE                 Location/Qualifiers
source                  1..11
                        mol_type = protein
                        organism = synthetic construct
SEQUENCE: 401
FCGFPSCSTS C                                                          11

SEQ ID NO: 402          moltype = AA  length = 12
FEATURE                 Location/Qualifiers
source                  1..12
                        mol_type = protein
                        organism = synthetic construct
SEQUENCE: 402
CTPPSCCQLH HA                                                         12

SEQ ID NO: 403          moltype =   length =
SEQUENCE: 403
000

SEQ ID NO: 404          moltype =   length =
SEQUENCE: 404
000

SEQ ID NO: 405          moltype =   length =
SEQUENCE: 405
000

SEQ ID NO: 406          moltype =   length =
SEQUENCE: 406
000

SEQ ID NO: 407          moltype =   length =
SEQUENCE: 407
000

SEQ ID NO: 408          moltype =   length =
SEQUENCE: 408
000

SEQ ID NO: 409          moltype = AA  length = 10
FEATURE                 Location/Qualifiers
source                  1..10
                        mol_type = protein
                        organism = synthetic construct
SEQUENCE: 409
GGVCGPSPPC                                                            10

SEQ ID NO: 410          moltype =   length =
SEQUENCE: 410
000
```

```
SEQ ID NO: 411          moltype =   length =
SEQUENCE: 411
000

SEQ ID NO: 412          moltype = AA  length = 10
FEATURE                 Location/Qualifiers
source                  1..10
                        mol_type = protein
                        organism = synthetic construct
SEQUENCE: 412
CGPSPPCITT                                                10

SEQ ID NO: 413          moltype =   length =
SEQUENCE: 413
000

SEQ ID NO: 414          moltype =   length =
SEQUENCE: 414
000

SEQ ID NO: 415          moltype =   length =
SEQUENCE: 415
000

SEQ ID NO: 416          moltype =   length =
SEQUENCE: 416
000

SEQ ID NO: 417          moltype =   length =
SEQUENCE: 417
000

SEQ ID NO: 418          moltype =   length =
SEQUENCE: 418
000

SEQ ID NO: 419          moltype =   length =
SEQUENCE: 419
000

SEQ ID NO: 420          moltype =   length =
SEQUENCE: 420
000

SEQ ID NO: 421          moltype =   length =
SEQUENCE: 421
000

SEQ ID NO: 422          moltype =   length =
SEQUENCE: 422
000

SEQ ID NO: 423          moltype =   length =
SEQUENCE: 423
000

SEQ ID NO: 424          moltype =   length =
SEQUENCE: 424
000

SEQ ID NO: 425          moltype =   length =
SEQUENCE: 425
000

SEQ ID NO: 426          moltype =   length =
SEQUENCE: 426
000

SEQ ID NO: 427          moltype =   length =
SEQUENCE: 427
000

SEQ ID NO: 428          moltype =   length =
SEQUENCE: 428
000
```

```
SEQ ID NO: 429          moltype =   length =
SEQUENCE: 429
000

SEQ ID NO: 430          moltype =   length =
SEQUENCE: 430
000

SEQ ID NO: 431          moltype =   length =
SEQUENCE: 431
000

SEQ ID NO: 432          moltype = AA  length = 10
FEATURE                 Location/Qualifiers
source                  1..10
                        mol_type = protein
                        organism = synthetic construct
SEQUENCE: 432
CEPAICEPSC                                                                 10

SEQ ID NO: 433          moltype =   length =
SEQUENCE: 433
000

SEQ ID NO: 434          moltype =   length =
SEQUENCE: 434
000

SEQ ID NO: 435          moltype =   length =
SEQUENCE: 435
000

SEQ ID NO: 436          moltype =   length =
SEQUENCE: 436
000

SEQ ID NO: 437          moltype =   length =
SEQUENCE: 437
000

SEQ ID NO: 438          moltype =   length =
SEQUENCE: 438
000

SEQ ID NO: 439          moltype =   length =
SEQUENCE: 439
000

SEQ ID NO: 440          moltype =   length =
SEQUENCE: 440
000

SEQ ID NO: 441          moltype =   length =
SEQUENCE: 441
000

SEQ ID NO: 442          moltype =   length =
SEQUENCE: 442
000

SEQ ID NO: 443          moltype =   length =
SEQUENCE: 443
000

SEQ ID NO: 444          moltype =   length =
SEQUENCE: 444
000

SEQ ID NO: 445          moltype =   length =
SEQUENCE: 445
000

SEQ ID NO: 446          moltype =   length =
SEQUENCE: 446
000
```

SEQ ID NO: 447 moltype = length =
SEQUENCE: 447
000

SEQ ID NO: 448 moltype = length =
SEQUENCE: 448
000

SEQ ID NO: 449 moltype = length =
SEQUENCE: 449
000

SEQ ID NO: 450 moltype = length =
SEQUENCE: 450
000

SEQ ID NO: 451 moltype = length =
SEQUENCE: 451
000

SEQ ID NO: 452 moltype = length =
SEQUENCE: 452
000

SEQ ID NO: 453 moltype = length =
SEQUENCE: 453
000

SEQ ID NO: 454 moltype = length =
SEQUENCE: 454
000

SEQ ID NO: 455 moltype = length =
SEQUENCE: 455
000

SEQ ID NO: 456 moltype = length =
SEQUENCE: 456
000

SEQ ID NO: 457 moltype = length =
SEQUENCE: 457
000

SEQ ID NO: 458 moltype = length =
SEQUENCE: 458
000

SEQ ID NO: 459 moltype = length =
SEQUENCE: 459
000

SEQ ID NO: 460 moltype = length =
SEQUENCE: 460
000

SEQ ID NO: 461 moltype = length =
SEQUENCE: 461
000

SEQ ID NO: 462 moltype = length =
SEQUENCE: 462
000

SEQ ID NO: 463 moltype = length =
SEQUENCE: 463
000

SEQ ID NO: 464 moltype = length =
SEQUENCE: 464
000

SEQ ID NO: 465 moltype = length =
SEQUENCE: 465
000

SEQ ID NO: 466 moltype = length =
SEQUENCE: 466
000

SEQ ID NO: 467 moltype = length =
SEQUENCE: 467
000

SEQ ID NO: 468 moltype = length =
SEQUENCE: 468
000

SEQ ID NO: 469 moltype = length =
SEQUENCE: 469
000

SEQ ID NO: 470 moltype = length =
SEQUENCE: 470
000

SEQ ID NO: 471 moltype = length =
SEQUENCE: 471
000

SEQ ID NO: 472 moltype = length =
SEQUENCE: 472
000

SEQ ID NO: 473 moltype = length =
SEQUENCE: 473
000

SEQ ID NO: 474 moltype = length =
SEQUENCE: 474
000

SEQ ID NO: 475 moltype = length =
SEQUENCE: 475
000

SEQ ID NO: 476 moltype = length =
SEQUENCE: 476
000

SEQ ID NO: 477 moltype = length =
SEQUENCE: 477
000

SEQ ID NO: 478 moltype = length =
SEQUENCE: 478
000

SEQ ID NO: 479 moltype = length =
SEQUENCE: 479
000

SEQ ID NO: 480 moltype = length =
SEQUENCE: 480
000

SEQ ID NO: 481 moltype = length =
SEQUENCE: 481
000

SEQ ID NO: 482 moltype = length =
SEQUENCE: 482
000

SEQ ID NO: 483 moltype = length =
SEQUENCE: 483
000

SEQ ID NO: 484 moltype = length =
SEQUENCE: 484
000

SEQ ID NO: 485 moltype = length =
SEQUENCE: 485
000

SEQ ID NO: 486 moltype = length =
SEQUENCE: 486
000

SEQ ID NO: 487 moltype = length =
SEQUENCE: 487
000

SEQ ID NO: 488 moltype = length =
SEQUENCE: 488
000

SEQ ID NO: 489 moltype = length =
SEQUENCE: 489
000

SEQ ID NO: 490 moltype = length =
SEQUENCE: 490
000

SEQ ID NO: 491 moltype = length =
SEQUENCE: 491
000

SEQ ID NO: 492 moltype = length =
SEQUENCE: 492
000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499
000

SEQ ID NO: 500 moltype = length =
SEQUENCE: 500
000

SEQ ID NO: 501 moltype = length =
SEQUENCE: 501
000

SEQ ID NO: 502 moltype = length =
SEQUENCE: 502
000

SEQ ID NO: 503 moltype = length =
SEQUENCE: 503
000

SEQ ID NO: 504 moltype = length =
SEQUENCE: 504
000

SEQ ID NO: 505 moltype = length =
SEQUENCE: 505
000

SEQ ID NO: 506 moltype = length =
SEQUENCE: 506
000

SEQ ID NO: 507 moltype = length =
SEQUENCE: 507
000

SEQ ID NO: 508 moltype = length =
SEQUENCE: 508
000

SEQ ID NO: 509 moltype = length =
SEQUENCE: 509
000

SEQ ID NO: 510 moltype = length =
SEQUENCE: 510
000

SEQ ID NO: 511 moltype = length =
SEQUENCE: 511
000

SEQ ID NO: 512 moltype = length =
SEQUENCE: 512
000

SEQ ID NO: 513 moltype = length =
SEQUENCE: 513
000

SEQ ID NO: 514 moltype = length =
SEQUENCE: 514
000

SEQ ID NO: 515 moltype = length =
SEQUENCE: 515
000

SEQ ID NO: 516 moltype = length =
SEQUENCE: 516
000

SEQ ID NO: 517 moltype = length =
SEQUENCE: 517
000

SEQ ID NO: 518 moltype = length =
SEQUENCE: 518
000

SEQ ID NO: 519 moltype = length =
SEQUENCE: 519
000

SEQ ID NO: 520 moltype = length =
SEQUENCE: 520
000

SEQ ID NO: 521 moltype = length =
SEQUENCE: 521
000

SEQ ID NO: 522 moltype = length =
SEQUENCE: 522
000

SEQ ID NO: 523 moltype = length =
SEQUENCE: 523
000

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

SEQ ID NO: 543 moltype = length =
SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =
SEQUENCE: 550
000

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = length =
SEQUENCE: 561
000

SEQ ID NO: 562 moltype = length =
SEQUENCE: 562
000

SEQ ID NO: 563 moltype = length =
SEQUENCE: 563
000

SEQ ID NO: 564 moltype = length =
SEQUENCE: 564
000

SEQ ID NO: 565 moltype = length =
SEQUENCE: 565
000

SEQ ID NO: 566 moltype = length =
SEQUENCE: 566
000

SEQ ID NO: 567 moltype = length =
SEQUENCE: 567
000

SEQ ID NO: 568 moltype = length =
SEQUENCE: 568
000

SEQ ID NO: 569 moltype = length =
SEQUENCE: 569
000

SEQ ID NO: 570 moltype = length =
SEQUENCE: 570
000

SEQ ID NO: 571 moltype = length =
SEQUENCE: 571
000

SEQ ID NO: 572 moltype = length =
SEQUENCE: 572
000

SEQ ID NO: 573 moltype = length =
SEQUENCE: 573
000

SEQ ID NO: 574 moltype = length =
SEQUENCE: 574
000

SEQ ID NO: 575 moltype = length =
SEQUENCE: 575
000

SEQ ID NO: 576 moltype = length =
SEQUENCE: 576
000

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582
000

SEQ ID NO: 583 moltype = length =
SEQUENCE: 583
000

SEQ ID NO: 584 moltype = length =
SEQUENCE: 584
000

SEQ ID NO: 585 moltype = length =
SEQUENCE: 585
000

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590
000

SEQ ID NO: 591 moltype = length =
SEQUENCE: 591
000

SEQ ID NO: 592 moltype = length =
SEQUENCE: 592
000

SEQ ID NO: 593 moltype = length =
SEQUENCE: 593
000

SEQ ID NO: 594 moltype = length =
SEQUENCE: 594
000

SEQ ID NO: 595 moltype = length =
SEQUENCE: 595
000

SEQ ID NO: 596 moltype = length =
SEQUENCE: 596
000

SEQ ID NO: 597 moltype = length =
SEQUENCE: 597
000

SEQ ID NO: 598 moltype = length =
SEQUENCE: 598
000

SEQ ID NO: 599 moltype = length =
SEQUENCE: 599
000

SEQ ID NO: 600 moltype = length =
SEQUENCE: 600
000

SEQ ID NO: 601 moltype = length =
SEQUENCE: 601
000

SEQ ID NO: 602 moltype = length =
SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605
000

SEQ ID NO: 606 moltype = length =
SEQUENCE: 606
000

SEQ ID NO: 607 moltype = length =
SEQUENCE: 607
000

SEQ ID NO: 608 moltype = length =
SEQUENCE: 608
000

SEQ ID NO: 609 moltype = length =
SEQUENCE: 609
000

SEQ ID NO: 610 moltype = length =
SEQUENCE: 610
000

SEQ ID NO: 611 moltype = length =
SEQUENCE: 611
000

SEQ ID NO: 612 moltype = length =
SEQUENCE: 612
000

SEQ ID NO: 613 moltype = length =
SEQUENCE: 613
000

SEQ ID NO: 614 moltype = length =
SEQUENCE: 614
000

SEQ ID NO: 615 moltype = length =
SEQUENCE: 615
000

SEQ ID NO: 616 moltype = length =
SEQUENCE: 616
000

SEQ ID NO: 617 moltype = length =
SEQUENCE: 617
000

SEQ ID NO: 618 moltype = length =
SEQUENCE: 618
000

SEQ ID NO: 619 moltype = length =
SEQUENCE: 619
000

SEQ ID NO: 620 moltype = length =
SEQUENCE: 620
000

SEQ ID NO: 621 moltype = length =
SEQUENCE: 621
000

SEQ ID NO: 622 moltype = length =
SEQUENCE: 622
000

SEQ ID NO: 623 moltype = length =
SEQUENCE: 623
000

SEQ ID NO: 624 moltype = length =
SEQUENCE: 624
000

SEQ ID NO: 625 moltype = length =
SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =
SEQUENCE: 629
000

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

SEQ ID NO: 636 moltype = length =
SEQUENCE: 636
000

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =
SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

SEQ ID NO: 660 moltype = length =
SEQUENCE: 660
000

SEQ ID NO: 661 moltype = length =
SEQUENCE: 661
000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =
SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684
000

SEQ ID NO: 685 moltype = length =
SEQUENCE: 685
000

SEQ ID NO: 686 moltype = length =
SEQUENCE: 686
000

SEQ ID NO: 687 moltype = length =
SEQUENCE: 687
000

SEQ ID NO: 688 moltype = length =
SEQUENCE: 688
000

SEQ ID NO: 689 moltype = length =
SEQUENCE: 689
000

SEQ ID NO: 690 moltype = length =
SEQUENCE: 690
000

SEQ ID NO: 691 moltype = length =
SEQUENCE: 691
000

SEQ ID NO: 692 moltype = length =
SEQUENCE: 692
000

SEQ ID NO: 693 moltype = length =
SEQUENCE: 693
000

SEQ ID NO: 694 moltype = length =
SEQUENCE: 694
000

SEQ ID NO: 695 moltype = length =
SEQUENCE: 695
000

SEQ ID NO: 696 moltype = length =
SEQUENCE: 696
000

SEQ ID NO: 697 moltype = length =
SEQUENCE: 697
000

SEQ ID NO: 698 moltype = length =
SEQUENCE: 698
000

SEQ ID NO: 699 moltype = length =
SEQUENCE: 699
000

SEQ ID NO: 700 moltype = length =
SEQUENCE: 700
000

SEQ ID NO: 701 moltype = length =
SEQUENCE: 701
000

SEQ ID NO: 702 moltype = length =
SEQUENCE: 702
000

SEQ ID NO: 703 moltype = length =
SEQUENCE: 703
000

SEQ ID NO: 704 moltype = length =
SEQUENCE: 704
000

SEQ ID NO: 705 moltype = length =
SEQUENCE: 705
000

SEQ ID NO: 706 moltype = length =
SEQUENCE: 706
000

SEQ ID NO: 707 moltype = length =
SEQUENCE: 707
000

SEQ ID NO: 708 moltype = length =
SEQUENCE: 708
000

SEQ ID NO: 709 moltype = length =
SEQUENCE: 709
000

SEQ ID NO: 710 moltype = length =
SEQUENCE: 710
000

SEQ ID NO: 711 moltype = length =
SEQUENCE: 711
000

SEQ ID NO: 712 moltype = length =
SEQUENCE: 712
000

SEQ ID NO: 713 moltype = length =
SEQUENCE: 713
000

SEQ ID NO: 714 moltype = length =
SEQUENCE: 714
000

SEQ ID NO: 715 moltype = length =
SEQUENCE: 715
000

SEQ ID NO: 716 moltype = length =
SEQUENCE: 716
000

SEQ ID NO: 717 moltype = length =
SEQUENCE: 717
000

SEQ ID NO: 718 moltype = length =
SEQUENCE: 718
000

SEQ ID NO: 719 moltype = length =
SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740
000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748
000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754
000

SEQ ID NO: 755 moltype = length =
SEQUENCE: 755
000

SEQ ID NO: 756 moltype = length =
SEQUENCE: 756
000

SEQ ID NO: 757 moltype = length =
SEQUENCE: 757
000

SEQ ID NO: 758 moltype = length =
SEQUENCE: 758
000

SEQ ID NO: 759 moltype = length =
SEQUENCE: 759
000

SEQ ID NO: 760 moltype = length =
SEQUENCE: 760
000

SEQ ID NO: 761 moltype = length =
SEQUENCE: 761
000

SEQ ID NO: 762 moltype = length =
SEQUENCE: 762
000

SEQ ID NO: 763 moltype = length =
SEQUENCE: 763
000

SEQ ID NO: 764 moltype = length =
SEQUENCE: 764
000

SEQ ID NO: 765 moltype = length =
SEQUENCE: 765
000

SEQ ID NO: 766 moltype = length =
SEQUENCE: 766
000

SEQ ID NO: 767 moltype = length =
SEQUENCE: 767
000

SEQ ID NO: 768 moltype = length =
SEQUENCE: 768
000

SEQ ID NO: 769 moltype = length =
SEQUENCE: 769
000

SEQ ID NO: 770 moltype = length =
SEQUENCE: 770
000

SEQ ID NO: 771 moltype = length =
SEQUENCE: 771
000

SEQ ID NO: 772 moltype = length =
SEQUENCE: 772
000

SEQ ID NO: 773 moltype = length =
SEQUENCE: 773
000

SEQ ID NO: 774 moltype = length =
SEQUENCE: 774
000

SEQ ID NO: 775 moltype = length =
SEQUENCE: 775
000

SEQ ID NO: 776 moltype = length =
SEQUENCE: 776
000

SEQ ID NO: 777 moltype = length =
SEQUENCE: 777
000

SEQ ID NO: 778 moltype = length =
SEQUENCE: 778
000

SEQ ID NO: 779 moltype = length =
SEQUENCE: 779
000

SEQ ID NO: 780 moltype = length =
SEQUENCE: 780
000

SEQ ID NO: 781 moltype = length =
SEQUENCE: 781
000

SEQ ID NO: 782 moltype = length =
SEQUENCE: 782
000

SEQ ID NO: 783 moltype = length =
SEQUENCE: 783
000

SEQ ID NO: 784 moltype = length =
SEQUENCE: 784
000

SEQ ID NO: 785 moltype = length =
SEQUENCE: 785
000

SEQ ID NO: 786 moltype = length =
SEQUENCE: 786
000

SEQ ID NO: 787 moltype = length =
SEQUENCE: 787
000

SEQ ID NO: 788 moltype = length =
SEQUENCE: 788
000

SEQ ID NO: 789 moltype = length =
SEQUENCE: 789
000

SEQ ID NO: 790 moltype = length =
SEQUENCE: 790
000

SEQ ID NO: 791 moltype = length =
SEQUENCE: 791
000

SEQ ID NO: 792 moltype = length =
SEQUENCE: 792
000

SEQ ID NO: 793 moltype = length =
SEQUENCE: 793
000

SEQ ID NO: 794 moltype = length =
SEQUENCE: 794
000

SEQ ID NO: 795 moltype = length =
SEQUENCE: 795
000

SEQ ID NO: 796 moltype = length =
SEQUENCE: 796
000

SEQ ID NO: 797 moltype = length =
SEQUENCE: 797
000

SEQ ID NO: 798 moltype = length =
SEQUENCE: 798
000

SEQ ID NO: 799 moltype = length =
SEQUENCE: 799
000

SEQ ID NO: 800 moltype = length =
SEQUENCE: 800
000

SEQ ID NO: 801 moltype = length =
SEQUENCE: 801
000

SEQ ID NO: 802 moltype = length =
SEQUENCE: 802
000

SEQ ID NO: 803 moltype = length =
SEQUENCE: 803
000

SEQ ID NO: 804 moltype = length =
SEQUENCE: 804
000

SEQ ID NO: 805 moltype = length =
SEQUENCE: 805
000

SEQ ID NO: 806 moltype = length =
SEQUENCE: 806
000

SEQ ID NO: 807 moltype = length =
SEQUENCE: 807
000

SEQ ID NO: 808 moltype = length =
SEQUENCE: 808
000

SEQ ID NO: 809 moltype = length =
SEQUENCE: 809
000

SEQ ID NO: 810 moltype = length =
SEQUENCE: 810
000

SEQ ID NO: 811 moltype = length =
SEQUENCE: 811
000

SEQ ID NO: 812 moltype = length =
SEQUENCE: 812
000

SEQ ID NO: 813 moltype = length =
SEQUENCE: 813
000

SEQ ID NO: 814 moltype = length =
SEQUENCE: 814
000

SEQ ID NO: 815 moltype = length =
SEQUENCE: 815
000

SEQ ID NO: 816 moltype = length =
SEQUENCE: 816
000

SEQ ID NO: 817 moltype = length =
SEQUENCE: 817
000

SEQ ID NO: 818 moltype = length =
SEQUENCE: 818
000

SEQ ID NO: 819 moltype = length =
SEQUENCE: 819
000

SEQ ID NO: 820 moltype = length =
SEQUENCE: 820
000

SEQ ID NO: 821 moltype = length =
SEQUENCE: 821
000

SEQ ID NO: 822 moltype = length =
SEQUENCE: 822
000

SEQ ID NO: 823 moltype = length =
SEQUENCE: 823
000

SEQ ID NO: 824 moltype = length =
SEQUENCE: 824
000

SEQ ID NO: 825 moltype = length =
SEQUENCE: 825
000

SEQ ID NO: 826 moltype = length =
SEQUENCE: 826
000

SEQ ID NO: 827 moltype = length =
SEQUENCE: 827
000

SEQ ID NO: 828 moltype = length =
SEQUENCE: 828
000

SEQ ID NO: 829 moltype = length =
SEQUENCE: 829
000

SEQ ID NO: 830 moltype = length =
SEQUENCE: 830
000

SEQ ID NO: 831 moltype = length =
SEQUENCE: 831
000

SEQ ID NO: 832 moltype = length =
SEQUENCE: 832
000

SEQ ID NO: 833 moltype = length =
SEQUENCE: 833
000

SEQ ID NO: 834 moltype = length =
SEQUENCE: 834
000

SEQ ID NO: 835 moltype = length =
SEQUENCE: 835
000

SEQ ID NO: 836 moltype = length =
SEQUENCE: 836
000

SEQ ID NO: 837 moltype = length =
SEQUENCE: 837
000

SEQ ID NO: 838 moltype = length =
SEQUENCE: 838
000

SEQ ID NO: 839 moltype = length =
SEQUENCE: 839
000

SEQ ID NO: 840 moltype = length =
SEQUENCE: 840
000

SEQ ID NO: 841 moltype = length =
SEQUENCE: 841
000

SEQ ID NO: 842 moltype = length =
SEQUENCE: 842
000

SEQ ID NO: 843 moltype = length =
SEQUENCE: 843
000

SEQ ID NO: 844 moltype = length =
SEQUENCE: 844
000

SEQ ID NO: 845 moltype = length =
SEQUENCE: 845
000

SEQ ID NO: 846 moltype = length =
SEQUENCE: 846
000

SEQ ID NO: 847 moltype = length =
SEQUENCE: 847
000

SEQ ID NO: 848 moltype = length =
SEQUENCE: 848
000

SEQ ID NO: 849 moltype = length =
SEQUENCE: 849
000

SEQ ID NO: 850 moltype = length =
SEQUENCE: 850
000

SEQ ID NO: 851 moltype = length =
SEQUENCE: 851
000

SEQ ID NO: 852 moltype = length =
SEQUENCE: 852
000

SEQ ID NO: 853 moltype = length =
SEQUENCE: 853
000

SEQ ID NO: 854 moltype = length =
SEQUENCE: 854
000

SEQ ID NO: 855 moltype = length =
SEQUENCE: 855
000

SEQ ID NO: 856 moltype = length =
SEQUENCE: 856
000

SEQ ID NO: 857 moltype = length =
SEQUENCE: 857
000

SEQ ID NO: 858 moltype = length =
SEQUENCE: 858
000

SEQ ID NO: 859 moltype = length =
SEQUENCE: 859
000

SEQ ID NO: 860 moltype = length =
SEQUENCE: 860
000

SEQ ID NO: 861 moltype = length =
SEQUENCE: 861
000

SEQ ID NO: 862 moltype = length =
SEQUENCE: 862
000

SEQ ID NO: 863 moltype = length =
SEQUENCE: 863
000

SEQ ID NO: 864 moltype = length =
SEQUENCE: 864
000

SEQ ID NO: 865 moltype = length =
SEQUENCE: 865
000

SEQ ID NO: 866 moltype = length =
SEQUENCE: 866
000

SEQ ID NO: 867 moltype = length =
SEQUENCE: 867
000

SEQ ID NO: 868 moltype = length =
SEQUENCE: 868
000

SEQ ID NO: 869 moltype = length =
SEQUENCE: 869
000

SEQ ID NO: 870 moltype = length =
SEQUENCE: 870
000

SEQ ID NO: 871 moltype = length =
SEQUENCE: 871
000

SEQ ID NO: 872 moltype = length =
SEQUENCE: 872
000

SEQ ID NO: 873 moltype = length =
SEQUENCE: 873
000

SEQ ID NO: 874 moltype = length =
SEQUENCE: 874
000

SEQ ID NO: 875 moltype = length =
SEQUENCE: 875
000

SEQ ID NO: 876 moltype = length =
SEQUENCE: 876
000

SEQ ID NO: 877 moltype = length =
SEQUENCE: 877
000

SEQ ID NO: 878 moltype = length =
SEQUENCE: 878
000

SEQ ID NO: 879 moltype = length =
SEQUENCE: 879
000

SEQ ID NO: 880 moltype = length =
SEQUENCE: 880
000

SEQ ID NO: 881 moltype = length =
SEQUENCE: 881
000

SEQ ID NO: 882 moltype = length =
SEQUENCE: 882
000

SEQ ID NO: 883 moltype = length =
SEQUENCE: 883
000

SEQ ID NO: 884 moltype = length =
SEQUENCE: 884
000

SEQ ID NO: 885 moltype = length =
SEQUENCE: 885
000

SEQ ID NO: 886 moltype = length =
SEQUENCE: 886
000

SEQ ID NO: 887 moltype = length =
SEQUENCE: 887
000

SEQ ID NO: 888 moltype = length =
SEQUENCE: 888
000

SEQ ID NO: 889 moltype = length =
SEQUENCE: 889
000

SEQ ID NO: 890 moltype = length =
SEQUENCE: 890
000

SEQ ID NO: 891 moltype = length =
SEQUENCE: 891
000

SEQ ID NO: 892 moltype = length =
SEQUENCE: 892
000

SEQ ID NO: 893 moltype = length =
SEQUENCE: 893
000

SEQ ID NO: 894 moltype = length =
SEQUENCE: 894
000

SEQ ID NO: 895 moltype = length =
SEQUENCE: 895
000

SEQ ID NO: 896 moltype = length =
SEQUENCE: 896
000

SEQ ID NO: 897 moltype = length =
SEQUENCE: 897
000

SEQ ID NO: 898 moltype = length =
SEQUENCE: 898
000

SEQ ID NO: 899 moltype = length =
SEQUENCE: 899
000

SEQ ID NO: 900 moltype = length =
SEQUENCE: 900
000

SEQ ID NO: 901 moltype = length =
SEQUENCE: 901
000

SEQ ID NO: 902 moltype = length =
SEQUENCE: 902
000

SEQ ID NO: 903 moltype = length =
SEQUENCE: 903
000

SEQ ID NO: 904 moltype = length =
SEQUENCE: 904
000

SEQ ID NO: 905 moltype = length =
SEQUENCE: 905
000

SEQ ID NO: 906 moltype = length =
SEQUENCE: 906
000

SEQ ID NO: 907 moltype = length =
SEQUENCE: 907
000

SEQ ID NO: 908 moltype = length =
SEQUENCE: 908
000

SEQ ID NO: 909 moltype = length =
SEQUENCE: 909
000

SEQ ID NO: 910 moltype = length =
SEQUENCE: 910
000

SEQ ID NO: 911 moltype = length =
SEQUENCE: 911
000

SEQ ID NO: 912 moltype = length =
SEQUENCE: 912
000

SEQ ID NO: 913 moltype = length =
SEQUENCE: 913
000

SEQ ID NO: 914 moltype = length =
SEQUENCE: 914
000

SEQ ID NO: 915 moltype = length =
SEQUENCE: 915
000

SEQ ID NO: 916 moltype = length =
SEQUENCE: 916
000

SEQ ID NO: 917 moltype = length =
SEQUENCE: 917
000

SEQ ID NO: 918 moltype = length =
SEQUENCE: 918
000

SEQ ID NO: 919 moltype = length =
SEQUENCE: 919
000

SEQ ID NO: 920 moltype = length =
SEQUENCE: 920
000

SEQ ID NO: 921 moltype = length =
SEQUENCE: 921
000

SEQ ID NO: 922 moltype = length =
SEQUENCE: 922
000

SEQ ID NO: 923 moltype = length =
SEQUENCE: 923
000

SEQ ID NO: 924 moltype = length =
SEQUENCE: 924
000

SEQ ID NO: 925 moltype = length =
SEQUENCE: 925
000

SEQ ID NO: 926 moltype = length =
SEQUENCE: 926
000

SEQ ID NO: 927 moltype = length =
SEQUENCE: 927
000

SEQ ID NO: 928 moltype = length =
SEQUENCE: 928
000

SEQ ID NO: 929 moltype = length =
SEQUENCE: 929
000

SEQ ID NO: 930 moltype = length =
SEQUENCE: 930
000

SEQ ID NO: 931 moltype = length =
SEQUENCE: 931
000

SEQ ID NO: 932 moltype = length =
SEQUENCE: 932
000

SEQ ID NO: 933 moltype = length =
SEQUENCE: 933
000

SEQ ID NO: 934 moltype = length =
SEQUENCE: 934
000

SEQ ID NO: 935 moltype = length =
SEQUENCE: 935
000

SEQ ID NO: 936 moltype = length =
SEQUENCE: 936
000

SEQ ID NO: 937 moltype = length =
SEQUENCE: 937
000

SEQ ID NO: 938 moltype = length =
SEQUENCE: 938
000

SEQ ID NO: 939 moltype = length =
SEQUENCE: 939
000

SEQ ID NO: 940 moltype = length =
SEQUENCE: 940
000

```
SEQ ID NO: 941          moltype =   length =
SEQUENCE: 941
000

SEQ ID NO: 942          moltype =   length =
SEQUENCE: 942
000

SEQ ID NO: 943          moltype =   length =
SEQUENCE: 943
000

SEQ ID NO: 944          moltype =   length =
SEQUENCE: 944
000

SEQ ID NO: 945          moltype =   length =
SEQUENCE: 945
000

SEQ ID NO: 946          moltype =   length =
SEQUENCE: 946
000

SEQ ID NO: 947          moltype =   length =
SEQUENCE: 947
000

SEQ ID NO: 948          moltype =   length =
SEQUENCE: 948
000

SEQ ID NO: 949          moltype =   length =
SEQUENCE: 949
000

SEQ ID NO: 950          moltype =   length =
SEQUENCE: 950
000

SEQ ID NO: 951          moltype = AA  length = 10
FEATURE                 Location/Qualifiers
source                  1..10
                        mol_type = protein
                        organism = synthetic construct
SEQUENCE: 951
SCCAPVYCCK                                                    10

SEQ ID NO: 952          moltype =   length =
SEQUENCE: 952
000

SEQ ID NO: 953          moltype =   length =
SEQUENCE: 953
000

SEQ ID NO: 954          moltype =   length =
SEQUENCE: 954
000

SEQ ID NO: 955          moltype =   length =
SEQUENCE: 955
000

SEQ ID NO: 956          moltype =   length =
SEQUENCE: 956
000

SEQ ID NO: 957          moltype =   length =
SEQUENCE: 957
000

SEQ ID NO: 958          moltype =   length =
SEQUENCE: 958
000
```

SEQ ID NO: 959 moltype = length =
SEQUENCE: 959
000

SEQ ID NO: 960 moltype = length =
SEQUENCE: 960
000

SEQ ID NO: 961 moltype = length =
SEQUENCE: 961
000

SEQ ID NO: 962 moltype = length =
SEQUENCE: 962
000

SEQ ID NO: 963 moltype = length =
SEQUENCE: 963
000

SEQ ID NO: 964 moltype = length =
SEQUENCE: 964
000

SEQ ID NO: 965 moltype = length =
SEQUENCE: 965
000

SEQ ID NO: 966 moltype = length =
SEQUENCE: 966
000

SEQ ID NO: 967 moltype = length =
SEQUENCE: 967
000

SEQ ID NO: 968 moltype = length =
SEQUENCE: 968
000

SEQ ID NO: 969 moltype = length =
SEQUENCE: 969
000

SEQ ID NO: 970 moltype = length =
SEQUENCE: 970
000

SEQ ID NO: 971 moltype = length =
SEQUENCE: 971
000

SEQ ID NO: 972 moltype = length =
SEQUENCE: 972
000

SEQ ID NO: 973 moltype = length =
SEQUENCE: 973
000

SEQ ID NO: 974 moltype = length =
SEQUENCE: 974
000

SEQ ID NO: 975 moltype = length =
SEQUENCE: 975
000

SEQ ID NO: 976 moltype = length =
SEQUENCE: 976
000

SEQ ID NO: 977 moltype = length =
SEQUENCE: 977
000

SEQ ID NO: 978 moltype = length =
SEQUENCE: 978
000

SEQ ID NO: 979 moltype = length =
SEQUENCE: 979
000

SEQ ID NO: 980 moltype = length =
SEQUENCE: 980
000

SEQ ID NO: 981 moltype = length =
SEQUENCE: 981
000

SEQ ID NO: 982 moltype = length =
SEQUENCE: 982
000

SEQ ID NO: 983 moltype = length =
SEQUENCE: 983
000

SEQ ID NO: 984 moltype = length =
SEQUENCE: 984
000

SEQ ID NO: 985 moltype = length =
SEQUENCE: 985
000

SEQ ID NO: 986 moltype = length =
SEQUENCE: 986
000

SEQ ID NO: 987 moltype = length =
SEQUENCE: 987
000

SEQ ID NO: 988 moltype = length =
SEQUENCE: 988
000

SEQ ID NO: 989 moltype = length =
SEQUENCE: 989
000

SEQ ID NO: 990 moltype = length =
SEQUENCE: 990
000

SEQ ID NO: 991 moltype = length =
SEQUENCE: 991
000

SEQ ID NO: 992 moltype = length =
SEQUENCE: 992
000

SEQ ID NO: 993 moltype = length =
SEQUENCE: 993
000

SEQ ID NO: 994 moltype = length =
SEQUENCE: 994
000

SEQ ID NO: 995 moltype = length =
SEQUENCE: 995
000

SEQ ID NO: 996 moltype = length =
SEQUENCE: 996
000

SEQ ID NO: 997 moltype = length =
SEQUENCE: 997
000

SEQ ID NO: 998 moltype = length =
SEQUENCE: 998
000

SEQ ID NO: 999 moltype = length =
SEQUENCE: 999
000

SEQ ID NO: 1000 moltype = length =
SEQUENCE: 1000
000

SEQ ID NO: 1001 moltype = length =
SEQUENCE: 1001
000

SEQ ID NO: 1002 moltype = length =
SEQUENCE: 1002
000

SEQ ID NO: 1003 moltype = length =
SEQUENCE: 1003
000

SEQ ID NO: 1004 moltype = length =
SEQUENCE: 1004
000

SEQ ID NO: 1005 moltype = length =
SEQUENCE: 1005
000

SEQ ID NO: 1006 moltype = length =
SEQUENCE: 1006
000

SEQ ID NO: 1007 moltype = length =
SEQUENCE: 1007
000

SEQ ID NO: 1008 moltype = length =
SEQUENCE: 1008
000

SEQ ID NO: 1009 moltype = length =
SEQUENCE: 1009
000

SEQ ID NO: 1010 moltype = length =
SEQUENCE: 1010
000

SEQ ID NO: 1011 moltype = length =
SEQUENCE: 1011
000

SEQ ID NO: 1012 moltype = length =
SEQUENCE: 1012
000

SEQ ID NO: 1013 moltype = length =
SEQUENCE: 1013
000

SEQ ID NO: 1014 moltype = length =
SEQUENCE: 1014
000

SEQ ID NO: 1015 moltype = length =
SEQUENCE: 1015
000

SEQ ID NO: 1016 moltype = length =
SEQUENCE: 1016
000

SEQ ID NO: 1017 moltype = length =
SEQUENCE: 1017
000

SEQ ID NO: 1018 moltype = length =
SEQUENCE: 1018
000

SEQ ID NO: 1019 moltype = length =
SEQUENCE: 1019
000

SEQ ID NO: 1020 moltype = length =
SEQUENCE: 1020
000

SEQ ID NO: 1021 moltype = length =
SEQUENCE: 1021
000

SEQ ID NO: 1022 moltype = length =
SEQUENCE: 1022
000

SEQ ID NO: 1023 moltype = length =
SEQUENCE: 1023
000

SEQ ID NO: 1024 moltype = length =
SEQUENCE: 1024
000

SEQ ID NO: 1025 moltype = length =
SEQUENCE: 1025
000

SEQ ID NO: 1026 moltype = length =
SEQUENCE: 1026
000

SEQ ID NO: 1027 moltype = length =
SEQUENCE: 1027
000

SEQ ID NO: 1028 moltype = length =
SEQUENCE: 1028
000

SEQ ID NO: 1029 moltype = length =
SEQUENCE: 1029
000

SEQ ID NO: 1030 moltype = length =
SEQUENCE: 1030
000

SEQ ID NO: 1031 moltype = length =
SEQUENCE: 1031
000

SEQ ID NO: 1032 moltype = length =
SEQUENCE: 1032
000

SEQ ID NO: 1033 moltype = length =
SEQUENCE: 1033
000

SEQ ID NO: 1034 moltype = length =
SEQUENCE: 1034
000

SEQ ID NO: 1035 moltype = length =
SEQUENCE: 1035
000

SEQ ID NO: 1036 moltype = length =
SEQUENCE: 1036
000

SEQ ID NO: 1037 moltype = length =
SEQUENCE: 1037
000

SEQ ID NO: 1038 moltype = length =
SEQUENCE: 1038
000

SEQ ID NO: 1039 moltype = length =
SEQUENCE: 1039
000

SEQ ID NO: 1040 moltype = length =
SEQUENCE: 1040
000

SEQ ID NO: 1041 moltype = length =
SEQUENCE: 1041
000

SEQ ID NO: 1042 moltype = length =
SEQUENCE: 1042
000

SEQ ID NO: 1043 moltype = length =
SEQUENCE: 1043
000

SEQ ID NO: 1044 moltype = length =
SEQUENCE: 1044
000

SEQ ID NO: 1045 moltype = length =
SEQUENCE: 1045
000

SEQ ID NO: 1046 moltype = length =
SEQUENCE: 1046
000

SEQ ID NO: 1047 moltype = length =
SEQUENCE: 1047
000

SEQ ID NO: 1048 moltype = length =
SEQUENCE: 1048
000

SEQ ID NO: 1049 moltype = length =
SEQUENCE: 1049
000

SEQ ID NO: 1050 moltype = length =
SEQUENCE: 1050
000

SEQ ID NO: 1051 moltype = length =
SEQUENCE: 1051
000

SEQ ID NO: 1052 moltype = length =
SEQUENCE: 1052
000

SEQ ID NO: 1053 moltype = length =
SEQUENCE: 1053
000

SEQ ID NO: 1054 moltype = length =
SEQUENCE: 1054
000

SEQ ID NO: 1055 moltype = length =
SEQUENCE: 1055
000

SEQ ID NO: 1056 moltype = length =
SEQUENCE: 1056
000

SEQ ID NO: 1057 moltype = length =
SEQUENCE: 1057
000

SEQ ID NO: 1058 moltype = length =
SEQUENCE: 1058
000

SEQ ID NO: 1059 moltype = length =
SEQUENCE: 1059
000

SEQ ID NO: 1060 moltype = length =
SEQUENCE: 1060
000

SEQ ID NO: 1061 moltype = length =
SEQUENCE: 1061
000

SEQ ID NO: 1062 moltype = length =
SEQUENCE: 1062
000

SEQ ID NO: 1063 moltype = length =
SEQUENCE: 1063
000

SEQ ID NO: 1064 moltype = length =
SEQUENCE: 1064
000

SEQ ID NO: 1065 moltype = length =
SEQUENCE: 1065
000

SEQ ID NO: 1066 moltype = length =
SEQUENCE: 1066
000

SEQ ID NO: 1067 moltype = length =
SEQUENCE: 1067
000

SEQ ID NO: 1068 moltype = length =
SEQUENCE: 1068
000

SEQ ID NO: 1069 moltype = length =
SEQUENCE: 1069
000

SEQ ID NO: 1070 moltype = length =
SEQUENCE: 1070
000

SEQ ID NO: 1071 moltype = length =
SEQUENCE: 1071
000

SEQ ID NO: 1072 moltype = length =
SEQUENCE: 1072
000

SEQ ID NO: 1073 moltype = length =
SEQUENCE: 1073
000

SEQ ID NO: 1074 moltype = length =
SEQUENCE: 1074
000

SEQ ID NO: 1075 moltype = length =
SEQUENCE: 1075
000

SEQ ID NO: 1076 moltype = length =
SEQUENCE: 1076
000

SEQ ID NO: 1077 moltype = length =
SEQUENCE: 1077
000

SEQ ID NO: 1078 moltype = length =
SEQUENCE: 1078
000

SEQ ID NO: 1079 moltype = length =
SEQUENCE: 1079
000

SEQ ID NO: 1080 moltype = length =
SEQUENCE: 1080
000

SEQ ID NO: 1081 moltype = length =
SEQUENCE: 1081
000

SEQ ID NO: 1082 moltype = length =
SEQUENCE: 1082
000

SEQ ID NO: 1083 moltype = length =
SEQUENCE: 1083
000

SEQ ID NO: 1084 moltype = length =
SEQUENCE: 1084
000

SEQ ID NO: 1085 moltype = length =
SEQUENCE: 1085
000

SEQ ID NO: 1086 moltype = length =
SEQUENCE: 1086
000

SEQ ID NO: 1087 moltype = length =
SEQUENCE: 1087
000

SEQ ID NO: 1088 moltype = length =
SEQUENCE: 1088
000

SEQ ID NO: 1089 moltype = length =
SEQUENCE: 1089
000

SEQ ID NO: 1090 moltype = length =
SEQUENCE: 1090
000

SEQ ID NO: 1091 moltype = length =
SEQUENCE: 1091
000

SEQ ID NO: 1092 moltype = length =
SEQUENCE: 1092
000

SEQ ID NO: 1093 moltype = length =
SEQUENCE: 1093
000

SEQ ID NO: 1094 moltype = length =
SEQUENCE: 1094
000

SEQ ID NO: 1095 moltype = length =
SEQUENCE: 1095
000

SEQ ID NO: 1096 moltype = length =
SEQUENCE: 1096
000

SEQ ID NO: 1097 moltype = length =
SEQUENCE: 1097
000

SEQ ID NO: 1098 moltype = length =
SEQUENCE: 1098
000

SEQ ID NO: 1099 moltype = length =
SEQUENCE: 1099
000

SEQ ID NO: 1100 moltype = length =
SEQUENCE: 1100
000

SEQ ID NO: 1101 moltype = length =
SEQUENCE: 1101
000

SEQ ID NO: 1102 moltype = length =
SEQUENCE: 1102
000

SEQ ID NO: 1103 moltype = length =
SEQUENCE: 1103
000

SEQ ID NO: 1104 moltype = length =
SEQUENCE: 1104
000

SEQ ID NO: 1105 moltype = length =
SEQUENCE: 1105
000

SEQ ID NO: 1106 moltype = length =
SEQUENCE: 1106
000

SEQ ID NO: 1107 moltype = length =
SEQUENCE: 1107
000

SEQ ID NO: 1108 moltype = length =
SEQUENCE: 1108
000

SEQ ID NO: 1109 moltype = length =
SEQUENCE: 1109
000

SEQ ID NO: 1110 moltype = length =
SEQUENCE: 1110
000

SEQ ID NO: 1111 moltype = length =
SEQUENCE: 1111
000

SEQ ID NO: 1112 moltype = length =
SEQUENCE: 1112
000

SEQ ID NO: 1113 moltype = length =
SEQUENCE: 1113
000

SEQ ID NO: 1114 moltype = length =
SEQUENCE: 1114
000

SEQ ID NO: 1115 moltype = length =
SEQUENCE: 1115
000

SEQ ID NO: 1116 moltype = length =
SEQUENCE: 1116
000

SEQ ID NO: 1117 moltype = length =
SEQUENCE: 1117
000

SEQ ID NO: 1118 moltype = length =
SEQUENCE: 1118
000

SEQ ID NO: 1119 moltype = length =
SEQUENCE: 1119
000

SEQ ID NO: 1120 moltype = length =
SEQUENCE: 1120
000

SEQ ID NO: 1121 moltype = length =
SEQUENCE: 1121
000

SEQ ID NO: 1122 moltype = length =
SEQUENCE: 1122
000

SEQ ID NO: 1123 moltype = length =
SEQUENCE: 1123
000

SEQ ID NO: 1124 moltype = length =
SEQUENCE: 1124
000

SEQ ID NO: 1125 moltype = length =
SEQUENCE: 1125
000

SEQ ID NO: 1126 moltype = length =
SEQUENCE: 1126
000

SEQ ID NO: 1127 moltype = length =
SEQUENCE: 1127
000

SEQ ID NO: 1128 moltype = length =
SEQUENCE: 1128
000

SEQ ID NO: 1129 moltype = length =
SEQUENCE: 1129
000

-continued

```
SEQ ID NO: 1130        moltype =   length =
SEQUENCE: 1130
000

SEQ ID NO: 1131        moltype = AA  length = 11
FEATURE                Location/Qualifiers
source                 1..11
                       mol_type = protein
                       organism = synthetic construct
SEQUENCE: 1131
CQCSCCKPYC S                                                11
```

HAIR CLEANSER COMPOSITION, METHODS AND USES THEREOF

CROSS-REFERENCE

This application claims the benefit of U.S. Provisional Application No. 63/354,514, filed Jun. 22, 2022, which is hereby incorporated by reference in its entirety herein.

REFERENCE TO A SEQUENCE LISTING XML

This application contains a Sequence Listing which has been submitted electronically in XML format. The Sequence Listing XML is incorporated herein by reference. Said XML file, created on Jul. 17, 2023, is named 63230-712_201 SL.xml and is 232, 193 bytes in size.

BACKGROUND

Hair and scalp cleansing is a common grooming practice considered important for optimal hair cleanliness, health, and maintenance. Hair cleansers typically remove sebum, sweat, desquamated stratum corneum, and environmental dirt, which helps prevent development of conditions such as folliculitis and seborrheic dermatitis. Current commercial formulas employ synthetic detergents, technically described as surfactant systems, blended in varying quantities and ratios to achieve the desired amount of cleansing power. The cosmetic industry has provided consumers innumerable options that facilitate general hair cleansing, encompassing formulas with a broad variety of ingredients and compositions.

In addition to removing sebum, sweat, desquamated stratum corneum, and environmental dirt, a secondary function of shampoos is to impart a desired sensory effect to the hair. Hair that has been thoroughly cleaned—i.e., is completely devoid of any sebum or products tends to feel less smooth and look duller and as a result is generally not considered cosmetically desirable. One strategy to counter this problem is to incorporate a multitude of conditioners into the cleanser. These conditioners are deposited onto the hair surface, and generally modify surface properties of the hair only—improving the look and feel of hair—but do not address any underlying damage to the structure of hair. The excess deposition of these conditioning agents, especially when combined with inadequate cleansing, can cause the conditioners to accumulate in the hair and weigh hair down or make it appear duller. Thus, there is a need for new hair cleanser compositions which both cleans the hair and provides desired hair properties without excess deposition of conditioning agents.

SUMMARY

In one aspect, the present disclosure provides a hair cleanser composition for cleaning and repairing hair. In some embodiments, the hair cleanser composition comprises one or more solvents, one or more peptides, one or more hair conditioners, one or more skin conditioners, one or more cleansing agents; and one or more cosmetically or dermatologically acceptable excipients. In some embodiments, the one or more peptides comprises a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO:1131, or a combination thereof. In some embodiments, the one or more peptides comprises a peptide sequence comprising SEQ ID NO: 400, SEQ ID NO:

401, SEQ ID NO: 409, SEQ ID NO: 412, SEQ ID NO: 432, or a combination thereof. In some embodiments, the one or more peptides comprises a peptide sequence comprising SEQ ID NO: 400, SEQ ID NO: 409, SEQ ID NO: 412, or a combination thereof. In some embodiments, the one or more peptides comprises SEQ ID NO: 400. In some embodiments, the one or more peptides comprises SEQ ID NO: 409. In some embodiments, the one or more peptides comprises SEQ ID NO: 412.

In some embodiments, the concentration (% w/w) of the one or more peptides in the hair cleanser is between about 0.0001% to about 1%. In some embodiments, the concentration (% w/w) of the one or more peptides in the detoxifying hair and scalp cleanser is between about 0.0001% to about 0.01%. In some embodiments, the concentration (% w/w) of the one or more peptides in the detoxifying hair and scalp cleanser is between about 0.0001% to about 0.001%.

In some embodiments, the hair cleanser composition includes one or more hair conditioners selected from: panthenol, *Rubus ideaus* (raspberry) leaf extract, *Carthamus tinctorius* (safflower) seed extract, hydroxypropylgluconamide, hydroxypropylammonium gluconate, hydrolyzed hyaluronic acid, sodium hyaluronate, or combinations thereof. In some embodiments, the hair cleanser composition comprises panthenol.

In some embodiments, the hair cleanser composition includes one or more skin conditioners selected from: caprylyl glycol, maltooligosyl glucoside, hydrogenated starch hydrolysate, *Opuntia ficus-indica* stem extract, saccharide isomerase, alpha-glucan oligosaccharide, *Alteromonas* ferment extract, *Anetholea anisata* leaf extract, guar hydroxypropyltriammonium chloride, or combinations thereof. In some embodiments, the detoxifying hair and scalp cleanser composition includes one or more skin conditioners selected from: caprylyl glycol and guar hydroxypropyltriammonium chloride. In some embodiments, the one or more skin conditions comprises caprylyl glycol. In some embodiments, the one or more skin conditions comprises guar hydroxypropyltriammonium chloride.

In some embodiments, the hair cleanser composition includes one or more cleansing agents. In some embodiments, the one or more cleansing agents is a surfactant. In some embodiments, the surfactant is selected from: an anionic surfactant, an amphoteric surfactant, a non-ionic surfactant, a biosurfactant, or combinations thereof.

In some embodiments, the surfactant includes at least one anionic surfactant selected from: sodium methyl 2-sulfolaurate, sodium lauryl sulfoacetate, disodium 2-sulfolaurate, alkylbenzene sulfonates, ammonium lauryl sulfate, ammonium lauryl sulfate, ammonium xylenesulfonate, sodium $C_{14-16}$ olefin sulfonate, sodium cocoyl sarcosinate, sodium laureth sulfate, sodium lauryl sulfate, sodium lauryl sulfoacetate, sodium myreth sulfate, sodium xylenesulfonate, TEA-dodecylbenzenesulfonate, ethyl PEG-15 cocamine sulfate, dioctyl sodium sulfosuccinate, or combinations thereof. In some embodiments, the at least one anionic surfactant comprises sodium $C_{14-16}$ olefin sulfonate, sodium methyl 2-sulfolaurate, sodium lauryl sulfoacetate, or combinations thereof. In some embodiments, the at least one anionic surfactant comprises sodium $C_{14-16}$ olefin sulfonate. In some embodiments, the at least one anionic surfactant comprises sodium methyl 2-sulfolaurate. In some embodiments, the at least one anionic surfactant comprises sodium lauryl sulfoacetate.

In some embodiments, the surfactant includes at least one amphoteric surfactant selected from: cocamindopropyl hydroxysultaine, cocamidopropyl betaine, coco betaine, cocoamphoacetate, cocoamphodipropionate, disodium cocoamphodiacetate, disodium cocoamphodipropionate, lauroamphoacetate, sodium cocoyl isethionate, or combinations thereof. In some embodiments, at least one amphoteric surfactant comprises cocamidopropyl betaine.

In some embodiments, the hair cleanser composition includes one or more cosmetically or dermatologically acceptable excipients selected from: a humectant; a chelating agent; a buffer or a preservative, or combinations thereof.

In some embodiments, the humectant is selected from: glycerin, propylene glycol, propanediol, or isopentyldiol. In some embodiments, the humectant comprises glycerin.

In some embodiments, the chelating agent is selected from: sodium phytate, EDTA, sodium gluconate, trisodium dicarboxymethyl alaninate, tetrasodium glutamate diacetate, or caprylhydroxamic acid, or combinations thereof. In some embodiments, the chelating agent comprises caprylhydroxamic acid, sodium phytate, or combinations thereof. In some embodiments, the chelating agent comprises caprylhydroxamic acid. In some embodiments, the chelating agent comprises sodium phytate.

In some embodiments, the buffer is selected from: citric acid, lactic acid, glycolic acid, malic acid, tartaric acid, L-arginine, sodium hydroxide, potassium hydroxide, or combinations thereof. In some embodiments, the buffer comprises citric acid.

In some embodiments, the preservative is selected from: phenoxyethanol, caprylhydroxamic acid, potassium sorbate, ethylhexylglycerin, gluconolactone, sodium benzoate, benzoic acid, or combinations thereof. In some embodiments, the preservative comprises benzoic acid.

In some embodiments, the concentration (% w/w) of the one or more solvents in the hair cleanser composition is between about 50% to about 90%. In some embodiments, the concentration (% w/w) of the one or more hair conditioners in the hair cleanser composition is between about 0.01% to about 10%. In some embodiments, the concentration (% w/w) of the one or more skin conditioners in the hair cleanser composition is between about 0.01% to about 5%. In some embodiments, the concentration (% w/w) of the one or more cleansing agents in the hair cleanser composition is between about 0.1% to about 20%. In some embodiments, the concentration (% w/w) of the one or more cosmetically or dermatologically acceptable excipients in the hair cleanser composition is between about 0.1% to about 30%. In some embodiments, the one or more solvents comprises water.

In some embodiments, the pH of the hair cleanser composition is between about 4 and about 6. In some embodiments, the pH of the hair cleanser composition is about 4. In some embodiments, the pH of the hair cleanser composition is about 4.5. In some embodiments, the pH of the hair cleanser composition is about 5. In some embodiments, the pH of the hair cleanser composition is about 5.5. In some embodiments, the pH of the hair cleanser composition is about 6.

In another aspect, a method for cleansing hair using the hair cleanser composition described herein is provided.

Additional aspects and advantages of the present disclosure may become readily apparent to those skilled in this art from the following detailed description, wherein only illustrative embodiments of the present disclosure are shown and described. As may be realized, the present disclosure is capable of other and different embodiments, and its several details are capable of modifications in various obvious respects, all without departing from the disclosure.

DETAILED DESCRIPTION

Human hair fiber structure consists of cuticle, cortex and medulla. The cuticle consists of a thin overlapping layer of cells, like a system of scales, and provides protection for the inner core of the hair, known as the cortex. Cuticle cells are mechanically robust and are resistant to many environmental factors, including the penetration of foreign molecules, due to the high degree of isodipeptide and disulfide bonds present in its various lamellar layers. The cuticle represents roughly 15% of the weight of a strand of hair. The cortex is the middle region of the hair and represents about 80% of the weight of a strand of hair. The cortex is composed of hierarchal structures of elongated, fibrous alpha-helical keratin extending along the fiber axis embedded in an amorphous protein matrix. It is the cortex with its system of intertwined protein fibers and supporting matrix that gives hair its tensile properties (strength, elasticity). A cell membrane complex joins cuticle cells with other cuticle cells, cortical cells with other cortical cells, and cuticle cells with cortical cells. The medulla corresponds to a central beam of cells and is absent in some hair fibers.

Human hair comprises approximately 65% to 95% protein. Proteins exhibit their active properties within specific temperature and pH value ranges and can unfold beyond these limits. Thermal denaturation for fibrous hard alpha-keratin proteins, i.e., the cortical proteins responsible for hair strength and elasticity, show a significant increase in stability when treated with low pH solution. This is particularly true for those with oxidative damage, such as by bleaching, and has been evidenced by a significant increase in enthalpy and peak temperature of thermal denaturation as quantified by DSC. Enthalpy is generally understood to reflect the quantity and structural integrity of alpha-helical material in hair intermediate filaments (IFs), while the peak temperature reflects the cross-link density of the matrix in which IFs are embedded. This phenomenon is further supported by amino acid analysis, X-ray diffraction, Raman spectroscopy, and tensile strength observations.

Alkaline pH creates a more favorable environment for cystine (disulfide) disruption as well as hydrolysis of amide bonds and formation of lanthionine and lysinoalanine—all of which weaken the hair's protein structure. Duration of the exposure of hair to solutions of a particular pH does not significantly change thermal stability; when compounded by the fact that tap water pH varies broadly from neutral to alkaline, this suggests that negative effects may be experienced in the duration of time for which hair is reasonably expected to be exposed during normal washing conditions.

The observed differences in thermal stability of hair proteins exposed to varied pH is due to a change in environment of the intermediate filaments, i.e., the interface between IFs and surrounding matrix proteins. This scaffolding structure at the IF surface is made by side chain interactions that anchor filaments to matrix. Strong adsorption of protons at the interface of the IFs may help shield this interface; disulfide bonds as well as electrostatic forces further stabilize this region.

During cleansing, the hair is in a structurally vulnerable state because water molecules break the hydrogen bonds that stabilize the protein structure. This causes swelling of certain parts of the cuticle and predisposes the hair fiber to damage. Further, it is established that the swelling behavior of the hair cuticle is highly dependent on pH: the more alkaline the environment, the greater the degree of swelling. Aside from the impact on thermal stability, this modification of cuticular swelling by pH has implications toward hair's properties and propensity for damage that is directly relevant for consumers. When the cuticle is swelled hair fibers have increased inter-fiber frictional force, resulting in increased tangling and a rough, unpleasant feel. Hair is also in a weaker state when wet; the need for greater comb force combined with the lower break stress of wet-state hair can easily lead to cuticle chipping, protein loss, and even critical breakage during hair washing and shampooing. Minimization of cuticle swelling exhibited at acidic pH may help offset this effect.

Proteins in hair are in an optimal state (most structurally resilient) around a pH of 5. This more acidic pH environment also minimizes excess swelling of the cuticle, reducing protein loss, preserving color, and minimizing electrostatic repulsion. This is also the ideal pH range for skin, which has an acidic mantle. Skin that has a disrupted pH can experience barrier perturbation, inflammation, and irritation. The pH of tap waters varies significantly from 6.5-9.53 and can contain metal ions like divalent calcium and magnesium (hard water minerals) which impact hair texture as well as trace levels of transition metals like copper, iron, nickel, lead, and others that can contribute to oxidative degradation of the hair fiber.

Further, peptides may be used to treat damaged hair during cleansing. These peptides may interact with the hair primarily via covalent (disulfide) bonds, polar bonds, and hydrophobic interactions. However, penetration of the peptide into the cortex of the hair strands, which is necessary for successful treatment, can be difficult. Molecular size and polarity play a large role in determining the ability of a molecule to gain access to the interior of the fiber structure. Further, the presence of sebum and products on the hair stands impedes the ability of the peptide to migrate successfully to the cortex. While appropriately acidic pH aids in the stabilization of hair's protein structure as specified above, these peptides may work in a complementary and synergistic way to add additional reinforcement. Taken together, this system provides both protection and repair of hair's protein structure which can be vulnerable during the washing process.

Accordingly, provided herein is a hair cleanser composition having an optimized pH that reduces swelling and protein loss. Formulating a shampoo at more acidic pH can help counteract this alkaline pH environment and minimize the net negative charge on hair proteins, which minimizes cuticle swelling and also reduces binding sites for dissolved metal cations. While having protective agents like emollients, occlusives, cationics, and polymers on the hair fiber minimizes friction and associated styling damage and provides a barrier to heat, UV, and pollution, excessive product build-up which can weigh hair down and prevent additional products from performing as well. The hair compositions may include peptides which reinforce the protein structure within the hair cortex to restore tensile strength to hair fibers. These peptides may not be compatible with traditional conditioning agents that form a film or coating and can block the peptide from interacting with hair proteins and most especially from entry to the cortex.

In some embodiments, the hair cleanser compositions described herein comprise low molecular weight peptides capable of penetrating to the cortex of the hair and improving the mechanical properties of hair. In some embodiments, the hair cleanser compositions described herein provide a long-lasting improved texture and improved manageability to the hair when dried. After prolonged use, the hair cleanser compositions described herein provide the hair with soft, shiny, undamaged texture and with the other desired features. The hair cleanser compositions described herein do not strip the hair of any essential oils, mitigates protein loss, and repairs the underlying hair damage, thus avoiding excess reliance on conditioners that coat the hair fiber to achieve desired properties. Further, due to their limited ingredients, the hair cleanser compositions described herein do not contribute to the build-up of excess conditioning agents or other products that can ultimately weigh hair down.

In some embodiment, the hair cleanser composition provided herein comprise one or more solvents, one or more peptides, one or more hair conditioners, one or more skin conditioners, one or more cleansing agents, and one or more cosmetically or dermatologically acceptable excipients. In some embodiments, the one or more peptides have a peptide sequence from 6 to 15 amino acids. In some embodiments, from 2 to 5 amino acids of the peptide sequence are cysteines. The composition of the peptides provides improved resistance, strength, toughness, and elasticity to the hair.

The hair cleanser composition described herein cleans the hair while maintaining an optimum pH environment of hair to minimize fiber swelling and preserve structural integrity. Additionally, the hair cleanser compositions clean the scalp while maintaining an optimum pH environment to avoid over drying the scalp and without disrupting the natural barrier function of the scalp. The hair cleanser compositions described herein have a pH optimized to cleanse the hair and scalp. In some embodiments, the pH of the hair cleanser composition is optimized to promote the efficacy of certain ingredients in the compositions. In some embodiments, the pH of the hair cleanser composition is optimized to promote the efficacy of salicylic acid. In some embodiments, the pH of the composition is optimized to promote chelation of certain minerals and metals. In some embodiments, the pH of the composition is optimized to minimize swelling of the cuticle. In some embodiments, reduced swelling of the cuticle reduces tangling of the hair. In some embodiments, the pH of the composition is optimized to protect the structural integrity of the hair and mitigate protein and lipid loss.

In some embodiments, the hair cleanser composition has a pH between about 1 to about 7. In some embodiments, the hair cleanser composition has a pH of about 1, about 1.25 about 1.5, about 1.75, about 2, about 2.25, about 2.5, about 2.75, about 3, about 3.25, about 3.5, about 3.75, about 4, about 4.25, about 4.5, about 4.75, about 5, about 5.25, about 5.5, about 5.75, about 6, about 6.25, about 6.5, about 6.75, about 7, and any values therebetween. In some embodiments, the hair cleanser composition has a pH between about 1 to about 7, between about 2 to about 7, between about 3 to about 7, between about 3.5 to about 7, between about 4 to about 7, between about 4 to about 6.

Definitions

Unless defined otherwise, all terms of art, notations, and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range of formats. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, a description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including combinations thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative, or quantitative and qualitative determinations. Assessing can be relative or absolute. "Detecting the presence of" can include determining the amount of something present in addition to determining whether it is present or absent depending on the context.

The term "about" or "approximately" as used herein when referring to a measurable value such as an amount or concentration and the like, is meant to encompass variations of 20%, 10%, 5%, 1%, 0.5%, or even 0.1% of the specified amount. For example, "about" can mean plus or minus 10%, per the practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, up to 5-fold, or up to 2-fold, of a value. Where particular values can be described in the application and claims, unless otherwise stated the term "about" may be assumed to encompass the acceptable error range for the particular value. Also, where ranges, subranges, or both, of values can be provided, the ranges or subranges can include the endpoints of the ranges or subranges.

Where values are described as ranges, it may be understood that such disclosure includes the disclosure of all possible sub-ranges within such ranges, as well as specific numerical values that fall within such ranges irrespective of whether a specific numerical value or specific sub-range is expressly stated.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As used herein, the term "mixture" or "mixtures" is meant to include a simple combination of materials and any compounds that may result from their combination.

As used herein, the term "cosmetically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, the term "cosmetically or dermatologically acceptable" refers to the compositions or components described are suitable for use in contact with human skin tissue without undue toxicity, incompatibility, instability, allergic response, and the like.

The section headings used herein are for organizational purposes only and are not to be construed as limiting the subject matter described.

Peptides

Keratin proteins may be lost when washed with a standard shampoo. Further, the pH of the hair during the washing may further contribute to protein loss due to swelling of the hair cuticle. The present application describes a hair cleanser composition that comprises peptides, which are based on the structure of keratin and keratin associated proteins. The peptides described herein bind hair with high affinity and repair keratinous fiber damage through the formation of disulfide bonds. The peptides have a sequence containing one or more cysteine amino acids that form disulfide bonds with free cysteine amino acids in the hair or keratins as well as participate in other types of bonding interactions that stabilize native hair proteins. The formation of new peptide-protein bonds helps to restore the mechanical properties of the hair fiber including elasticity, resistance, and appearance.

In some embodiments, the peptides described herein have a low molecular weight, between 6 to 15 amino acids, improving their ability to diffuse into the hair cortex to reduce protein damage and loss during repeated washing and chemical treatments and improve the physical and mechanical properties of the hair fibers.

In some embodiments, the peptides described herein include hydrophobic residues for added hydrophobicity and improved affinity to hair proteins. In some embodiments, the peptides described herein include polar residues for added hydrophilicity and improved affinity to hair proteins.

In some embodiments, each of the peptide sequences described herein are used separately or in combination, as well as all or part of the peptide sequence. In some embodiments, the hair cleanser composition comprises at least one or more peptide sequences. In some embodiments, the hair cleanser composition comprises at least two or more peptide sequences. In some embodiments, the hair cleanser composition comprises at least three or more peptide sequences. In other embodiments, the hair cleanser composition comprises at least four or more peptide sequences.

The number of amino acids of the peptide sequence is from 6 to 15. In some embodiments, the number of amino acids of the peptide sequence is 6. In some embodiments, the number of amino acids of the peptide sequence is 7. In some embodiments, the number of amino acids of the peptide sequence is 8. In some embodiments, the number of amino acids of the peptide sequence is 9. In some embodiments, the number of amino acids of the peptide sequence is 10. In some embodiments, the number of amino acids of the peptide sequence is 11. In some embodiments, the number of amino acids of the peptide sequence is 12. In some embodiments, the number of amino acids of the peptide sequence is 13. In some embodiments, the number of amino acids of the peptide sequence is 14. In some embodiments, the number of amino acids of the peptide sequence is 15.

In some embodiments, each peptide sequence contains amino acids comprising sulfur. In some embodiments, the peptide sequence comprises cysteine amino acids, that interact with the hair and allows the formation of intermolecular cross-linking, stabilizing the keratinous fiber. In some embodiments, the hair cleanser composition described herein comprises peptide sequences with high cysteine content to enrich the properties of the hair, such as to improve elasticity and resistance, reduce putative damage of the hair, improve and/or change hair characteristics. In some embodiments, cysteine comprises 10% to 50% of the total amount of amino acids of the peptide sequence. In some embodiments, the peptide sequence comprises 2 cysteines. In some embodiments, the peptide sequence comprises 3 cysteines. In some embodiments, the peptide sequence comprises 4 cysteines. In some embodiments, the peptide sequence comprises 5 cysteines.

In some embodiments, the peptides comprise a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO: 951, SEQ ID NO:1131, or combinations thereof. In some embodiments, the peptides comprise a peptide sequence comprising at least 90%, 91%, 92%, 93%, 94%, 95%, 96%, 97%, 98%, 99%, or 100% of SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO: 951, SEQ ID NO:1131, or combinations thereof.

TABLE 1

Sequences of peptides

| SEQ ID NO | Sequences |
|---|---|
| 75 | CLPCL PAASC |
| 400 | GGV CGPSP PCITT |
| 401 | F CGFPS CSTSC |
| 402 | CT PPSCC QLHHA |
| 409 | GGVCG PSPPC |
| 412 | CGPSP PCITT |
| 432 | CEPAI CEPSC |
| 951 | SCCAP VYCCK |
| 1131 | C QCSCC KPYCS |

The concentration of the peptide to be used depends on several factors, such as the condition of the hair, the origin of the hair, and the hair treatment formulation. The peptides described herein can be prepared by conventional methods of peptide synthesis, well known in the state of the art. In some embodiments, the concentration (% w/w) of the one or more peptides in the hair cleanser composition is between about 0.0001% to about 1.0%. In some embodiments, the concentration of the peptide in the hair cleanser composition is about 0.0001%, about about 0.0010%, about 0.0015%, about 0.0020%, about 0.0025%, about 0.0030%, about 0.0035%, about 0.0040%, about 0.0045%, about 0.0050%, about 0.0055%, about about 0.0065%, about 0.0070%, about 0.0075%, about 0.0080%, about 0.0085%, about 0.0090%, about 0.0095%, about 0.01%, about 0.05%, about 0.055%, about 0.060%, about about 0.070%, about 0.075%, about 0.080%, about 0.085%, about 0.090%, about about 0.1%, about 0.15%, about 020%, about 0.25%, about 0.30%, about 0.35%, about about 0.45%, about 0.50%, about 0.55%, about 0.60%, about 0.65%, about 0.70%, about about 0.80%, about 0.85%, about 0.90%, about 0.95%, about 1.0%, and any values therebetween. In some embodiments, the concentration of the peptide in the hair cleanser composition is between about 0.0001% to about 0.95%, between about 0.0005% to about 0.9%, between about 0.001% to about 0.85%, between about 0.005% to about 0.8%, between about to about 0.75%, between about 0.050% to about 0.70%, between about 0.10% to about between about 0.15% to about 0.60%, between about 0.20% to about 0.55%, between about 0.25% to about 0.50%, between about 0.30% to about 0.45%, between about 0.35% to about 0.40%, and between about 0.40% to about 1.0%.

The hair cleanser compositions described herein enrich and improve the properties and characteristics of the hair, such as elasticity, strength, pH, structural integrity, appearance, and feel, repairing and/or preserving damaged keratinous fiber. The hair cleanser composition described herein increases resistance due to the presence of the cysteine-rich peptides of the composition, even after several rinsing's. The hair cleanser compositions described herein acts as an effective cleanser without the associated harshness of other compositions in the art, at a hair-appropriate pH, and without excessive use of conditioning agents. In the context of the present disclosure, the hair cleanser composition can also be applied to the hair as, but not limited to, an aqueous solution or conventional shampoo or conditioner.

Hair Conditioners

The hair cleanser composition described herein includes one or more hair conditioners which repair and improve the properties of hair, such as elasticity, resistance, texture (i.e., softness, smoothness, etc.), and appearance. In some embodiments, the hair cleanser composition comprises one or more hair conditioners selected from: panthenol, salicylic acid, sodium salicylate, carnosine, tetrahexyldecyl ascorbate, hyaluronic acid/sodium hyaluronate, hydrolyzed hyaluronic acid, sarcosine, PCA, arginine PCA, brassicyl valinate esylate, brassicyl isoleucinate esylate, brassica alcohol, glycolipids, glycosphingolipids, sphinganine, *Rubus ideaus* (raspberry) leaf extract, bis-ethyl(isostearylimidazoline) isostearamide, *Camellia sinensis* leaf extract, *Carthamus tinctorius* (safflower) seed extract, *Glycine soja* (soybean) seed extract, *Elaeis guineensis* (palm) fruit extract, *Oryza sativa* (rice) extract, hydrolyzed *Adansonia digitata* seed extract, hydrolyzed corn starch, behenyl/stearyl aminopropanediol esters, C10-40 isoalkylamidopropylethyldimonium ethosulfate, *Linum usitatissimum* (linseed) extract, *Salva hispanica* seed extract, *Astrocaryum murumuru* fruit extract, *Moringa oleifera* seed extract, cinnamidopropyltrimonium chloride, hydroxypropyl guar hydroxypropyltrimonium chloride, *Trifolium pratense* (clover) flower extract, *Opuntia ficus-indica* stem extract, *Kappaphycus alvarezii* extract, *Laminaria saccharina* extract, guar hydroxypropyltriammonium chloride, bis-diglyceryl polyacyladipate-2, hydroxypropylgluconamide, hydroxypropylammonium gluconate, biosaccharide gum-4, *Prunus amygdalus dulcic* (sweet almond) seed extract, soybean glycerides, *Butyrospermum parkii* (shea) butter unsaponifiables, hydrolyzed chestnut extract, glyceryl rosinate, sodium methoxy peg-16 maleate/styrene sulfonate copolymer, panthenyl hydroxypropyl steardimonium chloride, and any combinations thereof.

In some embodiments, the concentration (% w/w) of the one or more hair conditioners in the hair cleanser composition is between about 0.01% to about 10.0%. In some embodiments, the concentration of the one or more hair conditioners in the hair cleanser is about 0.01%, about about 0.10%, about 0.15%, about 0.20%, about 0.25%, about 0.30%, about 0.35%, about about 0.45%, about 0.50%, about 0.55%, about 0.60%, about 0.65%, about 0.7%, about about 0.80%, about 0.85%, about 0.90%, about 0.95%, about 1.0%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, and any values therebetween. In some embodiments, the concentration of the one or more hair conditioners in the hair cleanser composition is between about 0.01% to about 10%, between about 0.05% to about 9.5%, between about 0.20% to about 9%, between about 0.30% to about 8.5%, between about 0.40% to about 8%, between about 0.50% to about 7.5%, between about to about 7%, between about 0.70% to about 6.5%, between about 0.80% to about 6%, between about 0.90% to about 5.5%, and between about 1% to about 5%.

Skin Conditioners

The hair cleanser composition described herein includes one or more skin conditioners which support the skin's barrier function and help retain moisture. In some embodiments, the hair cleanser composition comprises one or more skin conditioners selected from: niacinamide, allantoin, maltooligosyl glucoside, hydrogenated starch hydrolysate, *Opuntia ficus-indica* stem extract, sodium hyaluronate crosspolymer, jojoba esters, hydrolyzed jojoba esters, oleic acid, linoleic acid, linolenic acid, lactobionic acid, ursolic acid/sodium ursolate, nordihydroguaiaretic acid, ceramides, fructooligosaccharides, galactoarabinan, schizophyllan, *Anetholea anisate* leaf extract, *Tetraselmis suecica* extract, saccharide isomerase, *Alteromonas* ferment extract, *Pseudoalteromonas* ferment extract, *Corylus avellana* leaf extract, *Phyllanthus emblica* fruit extract, *Betula alba* juice, *Saccharum officinarum* (sugarcane) extract, *Rhodomyrtus tomentosa* fruit extract, *Hedychium coronarium* root extract, *Epilobium angustifolium* flower/leaf/stem extract, *Tremella fuciformis* sporocarp extract, alpha-glucan oligosaccharide, and any combinations thereof.

In some embodiments, the concentration (% w/w) of the one or more skin conditioners in the hair cleanser composition is between about 0.01% to about 5.0%. In some embodiments, the concentration of the one or more skin conditioners in the hair cleanser composition is about %, about 0.05%, about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.0%, and any values therebetween. In some embodiments, the concentration of the one or more skin conditioners in the hair cleanser composition is between about 0.01% to about 0.95%, between about 0.05% to about 1.0%, between about 0.20% to about 0.90%, between about 0.30% to about 0.85%, between about 0.40% to about 0.80%, between about 0.50% to about 0.75%, between about 0.60% to about 0.70%, and between about 0.70% to about 1.0%.

Cleansing Agents

The hair cleanser composition described herein includes one or more cleansing agents that help to clean the hair but do not remove or replace any essential oils. In some embodiments, the hair cleanser composition comprises one or more cleansing agents selected from: an anionic surfactant, an amphoteric surfactant, a non-ionic surfactant, a biosurfactant, and any combinations thereof.

In order to be cosmetically acceptable, the surfactants must provide good foaming profiles and a stable rheology in addition to being efficient cleansers. Anionic surfactants tend to be top performers in these categories; however, consumer perception of the most efficient traditionally employed classes (i.e., sulfates) has made reception of these challenging. While this limits the selection of appropriate surfactants, it must also be noted that a further limiting factor is ion tolerance—as mentioned previously, many surfactants tend to be neutral or alkaline, but an acidic composition demands performance and stability at low pH and in potentially hard water. Sulfonates, in particular alkyl sulfonates or olefin sulfonates, exemplify one class that meets the specified criteria. These surfactants exhibit particularly good synergy with alpha hydroxyl acids or salicylic acid.

However, single-surfactant systems often lack one aspect or another and it is preferential to utilize a blend. Amphoteric surfactants impart gentleness and improve sensory profiles. Hydroxysultaines possess a remarkably low irritation profile and improve the mildness of surfactant formulations while boosting foam and stability, permitting lower total surfactant levels—another critical criteria in formulations meant to respect the skin barrier of the scalp. They also exhibit notably broad pH and electrolyte tolerance, making them excellent cleansers in hard water and in combination with acidic ingredients. Amino acid-derived surfactants can cleanse while simultaneously moisturizing skin or conditioning hair and are yet another exemplary choice. These surfactants may be used daily on the hair or skin when formulated appropriately. Finally, biosurfactants represent yet another type of high-performing cleanser molecule that holds the added benefit of superior environmental compatibility, be that more sustainable source materials, improved biodegradability, or greener manufacturing.

In some embodiments, the one or more cleansing agents is an anionic surfactant selected from: sodium methyl 2-sulfolaurate, sodium lauryl sulfoacetate, disodium 2-sulfolaurate, alkylbenzene sulfonates, ammonium lauryl sulfate, ammonium xylenesulfonate, sodium laureth sulfate, sodium lauryl sulfate, sodium lauryl sulfoacetate, sodium 2-sulfolaurate, sodium myreth sulfate, sodium xylenesulfonate, sodium $C_{14-16}$ olefin sulfonate, sodium $C_{14-16}$ alpha olefin sulfonate, disodium lauryl sulfosuccinate, sodium methyl cocoyl taurate, sodium cocoyl isethionate, sodium lauryl isethionate, sodium cocoyl sarcosinate, sodium lauroyl sarcosinate, sodium myristoyl sarcosinate, lauroyl sarcosine, cocoyl sarcosine, myristoyl sarcosine, oleoyl sarcosine, myristoyl/stearoyl sarcosine, sodium lauroyl glutamate, sodium cocoyl glutamate, disodium cocoyl glutamate, cocoyl glutamic acid, lauroyl glutamic acid, potassium cocoyl glutamate, potassium lauroyl glutamate, potassium myristoyl glutamate, sodium myristoyl glutamate, sodium stearoyl glutamate, disodium stearoyl glutamate, sodium palmoyl glutamate, sodium lauroyl lactylate, sodium *Astrocaryum murumuruate*, sodium laurylglucosides hydroxypropylsulfonate, disodium laurylglucosides hydroxypropyl citrate, sodium hydroxypropylsulfonate laurylglucoside crosspolymer, dioctyl sodium sulfosuccinate, and any combinations thereof.

In some embodiments, the one or more cleansing agents is an amphoteric surfactant selected from: cocamindopropyl hydroxysultaine, cocamidopropyl betaine, coco betaine, betaine, cocoamphoacetate, cocoamphodipropionate, disodium cocoamphodiacetate, disodium cocoamphodipropionate, lauryl betaine, lauramidopropyl betaine, lauramidopropyl hydroxysultaine, lauryl hydroxysultaine, sodium dilauramidoglutamide lysine, sodium cocoamphopropionate, lauroamphoacetate, and any combinations thereof.

In some embodiments, the one or more cleansing agents is a non-ionic surfactant selected from: decyl glucoside, lauryl glucoside, coco-glucoside, cocoyl methyl glucamide, capryloyl/caproyl methyl glucamide, lauroyl/myristoyl methyl glucamide, cocamidopropylamine oxide, decylamine oxide, and combinations thereof.

In some embodiments, the one or more cleansing agents is a biosurfactant selected from: *Sapindus mukorossi* (soapnut) extract, saponin, lipopeptide, canola sophorolipid, potassium cocoyl hydrolyzed oat protein, *Starmella bombicola/Brassica* oil ferment, glycoside, glycolipid, rhamnolipid, phospholipid, sophorolipid, and any combinations thereof.

In some embodiments, the concentration (% w/w) of the one or more cleansing agents in the hair cleanser composition is between about 0.1% to about 20%. In some embodiments, the concentration of the one or more cleansing agents in the hair cleanser composition is about 0.1%, about 0.2%, about 0.3%, about 0.4%, about 0.5%, about 0.6%, 0.7%, about 0.8%, about 0.9%, about 1.0%, about 1.2%, about 1.4%, about 1.6%, about 1.8%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about about 11.0%, about 11.5%, about 12.0%, about 12.5%, about 13%, about 13.5%, about 14%, about 14.5%, about 15%, about 16%, about 17%, about 18%, about 19%, about 20%, and any values therebetween. In some embodiments, the concentration of the one or more cleansing agents in the hair cleanser composition is between about 0.1% to about 20%, between about to about 19%, between about 0.3% to about 18%, between about 0.4% to about 17%, between about 0.5% to about 16%, between about 0.6% to about 15%, between about 0.7% to about 14.5%, between about 0.8% to about 14%, between about 0.9% to about 13.5%, between about 1.0% to about 13%, between about 1.5% to about 12.5%, between about 2.0% to about 12%, between about 2.5% to about 11.5%, between about 3.0% to about 11%, between about 3.5% to about 10.5%, and between about 4% to about 10%.

Excipients

The hair cleanser composition described herein includes one or more cosmetically or dermatologically acceptable excipients. The cosmetically or dermatologically acceptable excipients includes, but are not limited to, preservatives, antioxidants, thickeners, chelating agents, co-solvents, sunscreen agents, vitamins, dyes, hair coloring agents, proteins, amino acids, organic polymers, natural extracts such as plant extracts, humectants, fragrances, perfumes, oils, emollients, lubricants, butters, penetrants, thickeners, viscosity modifiers, polymers, resins, hair fixatives, silicones, film formers, surfactants, detergents, emulsifiers, opacifying agents, volatiles, propellants, liquid vehicles, carriers, salts, pH adjusting agents (buffers), neutralizing agents, buffers, hair conditioning agents, anti-static agents, anti-frizz agents, anti-dandruff agents, absorbents, and any combinations thereof.

In some embodiments, the concentration (% w/w) of the one or more cosmetically or dermatologically acceptable excipients in the hair cleanser composition is between about 0.1% to about 30%. In some embodiments, the concentration of the one or more cosmetically or dermatologically acceptable excipients in the hair cleanser composition is about 0.1%, about about 1.0%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 21.0%, about 22.0%, about 23.0%, about 24.0%, about 25.0%, about 26.0%, about 27.0%, about 28.0%, about 29.0%, about 30.0%, and any values therebetween. In some embodiments, the concentration of the one or more cosmetically or dermatologically acceptable excipients in the hair cleanser composition is between about 0.1% to about 29.0%, between about 0.5% to about 28.0%, between about 1.0% to about 27.0%, between about 2.0% to about 26.0%, between about 3.0% to about 25.0%, between about 4.0% to about 24.0%, between about 5.0% to about 23.0%, between about 6.0% to about 22.0%, between about 7.0% to about 21.0%, between about 8.0% to about 20.0%, between about 9.0% to about 19.0%, between about 10.0% to about 18.0%, between about 11.0% to about 17.0%, between about 12.0% to about 16.0%, between about 13.0% to about 15.0%, between about 14.0% to about 14.5%, and between about 14.5% to about 30.0%.

In some embodiments, the one or more cosmetically or dermatologically acceptable excipients is an emulsifier selected from: caprylic/capric/diglyceryl succinate, C14-16 glycol palmitate, C18-20 glycol isostearate, cocamidopropyl lauryl ether, dipentaerythrityl hydroxystearate, dipentaerythrityl hydroxyisostearate, dipentaerythrityl hexacaprate/caprylate, palm kernel glycerides, lecithin, hydrogenated lecithin, phosphatidylcholine, C12-16 alcohols, palmitic acid, glyceryl behenate, glyceryl stearate, glyceryl stearate citrate, glyceryl oleate citrate, sorbitan laurate, lauryl laurate, sorbitan olivate, cetearyl olivate, glyceryl stearate citrate, sodium stearoyl lactylate, sodium stearoyl glutamate, sodium cocoyl glutamate, caprylyl/capryl glucoside, polyhydroxystearic acid, phenethyl alcohol, sodium surfactin, polyglycerin-3, polyglyceryl-3 distearate, polyglyceryl-3 diisostearate, polyglyceryl-3 cocoate, polyglyceryl-3 dicitrate/stearate, polyglyceryl-3 beeswax, polyglyceryl-3 polyricinoleate, polyglyceryl-4 oleate, polyglyceryl-4 caprate, polylgylceryl-4 laurate, polyglyceryl-6 caprylate, polyglyceryl-6 stearate, polyglyceryl-6 distearate, polyglyceryl-6 behenate, polyglyceryl-6 polyhydroxystearate, polyglyceryl-6 oleate, polyglyceryl-6 ricinoleate, polyglyceryl-6 polyricinoleate, polyglyceryl-10 laurate, candelilla/jojoba/rice bran polyglyceryl-3 esters, stearoyl glutamic acid, Polysorbate-20, polyglyceryl-10 laurate, polyglyceryl-6 caprylate, polyglyceryl-3 cocoate, polyglyceryl-4 caprate, polyglyceryl-6 ricinoleate, polyglyceryl-6 caprylate, sodium surfactin, and any combinations thereof.

In some embodiments, the one or more cosmetically or dermatologically acceptable excipients is a chelating agent selected from: phytic acid, sodium phytate, caprylhydroxamic acid, trisodium dicarboxymethyl alaninate, gluconic acid, sodium gluconate, pentasodium pentetate, sodium carboxymethyl inulin, tetrasodium glutamate diacetate, trisodium ethylenediamine succinate, sodium thiosulfate, diiospropyl oxalate, disodium EDTA, disodium EDTA-copper, HEDTA, oxalic acid, potassium citrate, sodium citrate, dodium oxalate, TEA-EDTA, tetrasodium EDTA, trisodium EDTA, trisodium HEDTA, and any combinations thereof.

In some embodiments, the one or more cosmetically or dermatologically acceptable excipients is a preservative selected from: benzoic acid, butyl paraben, diazolidinyl urea, DMDM hydantoin, ethyl paraben, imidazolidinyl urea, iodopropynyl butylcarbamate, isobutyl paraben, methyl paraben, methylchloroisothiazolinone, methylisothiazolinone, phenoxyethanol, propyl paraben, sodium benzoate, potassium sorbate, ethylhexylglycerin, gluconolactone, and any combinations thereof.

In some embodiments, the one or more cosmetically or dermatologically acceptable excipients is a thickener selected from: lauryl lactate, hydroxypropyl starch phosphate, acrylates copolymer, ammonium acryloyldimethyltaurate, sodium acryloyldimethyltaurate/VP copolymer, sodium acrylate/sodium acryloyldimethyl taurate copolymer, sodium polyacrylate, polyacrylate crosspolymer-11, carbomer, acrylates/C10-30 alkyl acrylate crosspolymer, hydroxyethyl acrylate/sodiumacryloyldimethyltaurate copolymer, lithium magnesium sodium silicate, sodium magnesium fluorosilicate, glycol distearate, hydrogenated castor oil, hydrogenated castor oil hydroxystearate, hydrogenated castor oil isostearate, hydrogenated castor oil stearate, hydrogenated castor PEG-8 esters, and any combinations thereof.

In some embodiments, the one or more cosmetically or dermatologically acceptable excipients is an anti-static agent. In some embodiments, the anti-static agent is a cationic surfactant selected from: quaternary ammonium compounds, behentrimonium chloride, behentrimonium methosulfate, cetrimonium chloride, cetrimonium methosulfate, benzalkonium chloride, benzethonium chloride, cinnamidopropyltrimonium chloride, cocotrimonium chloride, dicetyldimonium chloride, dicocodimonium chloride, laurtrimonium chloride, stearamidopropyl dimethylamine, steartrimonium chloride, stearalkonium chloride, tricetyldimonium chloride, PCA ethyl cocoyl arginate, C10-40 isoalkylamidopropylethyldimonium ethosulfate, dipalmitoylethyl hydroxyethylmonium methosulfate, shea butteramidopropyltrimonium chloride, and any combinations thereof.

In some embodiments, the one or more cosmetically or dermatologically acceptable excipients is a naturally derived polymer selected from: xanthan gum, pullulan, algin, *tetragonoloba* (guar) gum, *sclerotium* gum, acacia Senegal gum, cellulose, cellulose gum, carboxymethylcellulose, carbomer, hydroxypropyl starch phosphate, guar hydroxypropyltrimonium chloride, carboxymethyl hydroxyethyl cellulose, carboxymethyl hydroxypropyl guar, cellulose, ethyl cellulose, hydroxybutyl methylcellulose, hydroxyethylcellulose, hydroxymethylcellulose, lauryl polyglucose, and any combinations thereof.

In some embodiments, the one or more cosmetically or dermatologically acceptable excipients is an amino acid such as L-Cysteine.

In some embodiments, the one or more cosmetically or dermatologically acceptable excipients is a humectant selected from: 1,2,6 hexanetriol, dipropylene glycol, glycerin, butylene glycol, caprylyl glycol, pentylene glycol, isopentyldiol, hexylene glycol, panthenol, phytantriol, propylene glycol, propanediol, sodium PCA, sorbitol, triethylene glycol, polyglyceryl sorbitol, glucose, fructose, mannitol, xylitol, inositol, trehalose, polydextrose, potassium PCA, hydrogenated honey, hyaluronic acid, inositol, erythritol, capryl glycol, acetamidoethoxyethanol, and any combinations thereof.

In some embodiments, the one or more cosmetically or dermatologically acceptable excipients is a cationic polymer selected from: polyquaternium-10, polyquaternium-7, polyquaternium-11, polyquaternium-57, quaternium-15, quaternium-18, quaternium-22, quaternium-87, guar hydroxypropyltrimonium chloride, and any combinations thereof.

In some embodiments, the one or more cosmetically or dermatologically acceptable excipients is a non-ionic surfactant selected from: decyl glucoside, lauryl glucoside, coco-glucoside, cocoyl methyl glucamide, capryloyl/caproyl methyl glucamide, lauroyl/myristoyl methyl glucamide, cocamidopropylamine oxide, decylamine oxide, and combinations thereof. In some embodiments, the non-ionic surfactant is a solubilizer, emulsifier, stabilizer, emollient, thickener, and any combinations thereof.

In some embodiments, the one or more cosmetically or dermatologically acceptable excipients is a silicone selected from: amodimethicone, amodimethicone, dimethicone cyclomethicone, cyclopentasiloxane, dimethicone, dimethicone copolyol, dimethiconol, hydrolyzed wheat protein hydroxypropyl polysiloxane, trimethylsilylamodimethicone, and any combinations thereof.

In some embodiments, the one or more cosmetically or dermatologically acceptable excipients is a protein selected from: cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl silk amino acids, cocoyl hydrolyzed collagen, cocoyl hydrolyzed keratin, hydrolyzed keratin, hydrolyzed oat flour, hydrolyzed silk, hydrolyzed silk protein, hydrolyzed soy protein, hydrolyzed wheat protein, hydrolyzed quinoa, hydrolyzed elastin, hydrolyzed collagen, keratin, potassium cocoyl hydrolyzed collagen, and any combinations thereof.

In some embodiments, the one or more cosmetically or dermatologically acceptable excipients is a vitamin selected from: retinol, retinyl palmitate, ascorbic acid, tocopherol, tocopherol acetate, and any combinations thereof.

In some embodiments, the one or more cosmetically or dermatologically acceptable excipients is a natural extract selected from: Aloe barbadensis leaf extract, *Yucca schidigera* leaf extract, *Yucca schidigera* root extract, *Camellia sinensis* leaf extract, *Equisetum arvense* leaf extract, *Hamamelis virginiana* leaf extract, *Macrocystis pyrifera* kelp extract, and combinations thereof.

In some embodiments, the one or more cosmetically or dermatologically acceptable excipients is an emollient selected from: isopropyl lauroyl sarcosinate, phenethyl benzoate, C12-15 alkyl benzoate, caprylic/capric triglyceride, cetyl octanoate, octyldodecanol, dilinoleic acid/propanediol copolymer, isoamyl laurate, oleic acid, isohexadecane, squalane, isopropyl palmitate, polycitronellol, diheptyl succinate, capryloyl glycerin/sebacic acid copolymer, PPG-3 benzyl ether ethylhexanoate, hydrogenated vegetable oil, triheptanoin, diisopropyl sebacate, diisopropyl adipate, propylene glycol dibenzoate, propoxytetramethyl piperidinyl dimethicone, castor oil/IPDI copolymer, butylene glycol cocoate, butylene glycol dicaprylate/dicaprate (dispersant), propylene glycol dicaprylate/dicaprate, triolein (algae oil), propylene glycol dicaprylate/dicaprate, phytosteryl/octyldodecyl lauroyl glutamate, C10-18 triglycerides, isostearyl alcohol, diisostearyl malate, isoamyl laurate, *isoamyl cocoate, hemisqualane, polycitronellol acetate, ethyl macadamiate, coco-caprylate/caprate, coconut alkanes, C9-12 alkane, C13-15 alkane, C13-16 isoalkane, neopentyl glycol diheptanoate, hydrogenated ethylhexyl olivate, hydrogenated olive oil unsaponifiables, undecane, tridecane, isododecane, caprylyl caprylate/caprate, cetyl stearate, cetearyl stearate, decyl oleate, glyceryl stearate, glyceryl adipate, glyceryl arachidate, glyceryl arachidonate, glyceryl behenate, glyceryl caprate, glyceryl caprylate, glyceryl caprylate/caprate, glyceryl citrate/lactate/linoleate/oleate, glyceryl cocoate, glyceryl diarachidate, glyceryl dibehenate, glyceryl dierucate, glyceryl dihydroxystearate, glyceryl diisopalmitate, glyceryl diisostearate, glyceryl dilaurate, glyceryl dilinoleate, glyceryl dimyristate, glyceryl dioleate, glyceryl dipalmitate, glyceryl dipalmitoleate, glyceryl diricinoleate, glyceryl distearate, glyceryl erucate, glycol stearate, isocetyl stearate, isopropyl myristate, isopropyl palmitate, isopropyl stearate, isostearyl stearate, octyl palmitate, octyl stearate, propylene glycol dicaprylate/dicaprate, sorbitan benzoate, sorbitan caprylate, sorbitan isostearate, sorbitan laurate, sorbitan tristearate, stearyl stearate, tocopheryl linoleate, olive oil, avocado oil, coconut oil, sunflower oil, jojoba oil, argan oil, castor oil, almond oil, *Sesamum indicum* (sesame) seed oil, *Prunus areniaca* (apricot) kernel oil, *Crambe abyssinica* seed oil, *Oryza sativa* (rice) bran oil, *Vitis vinifera* (grape) seed oil, *Passiflora edulis* seed oil, meadowfoam seed oil, *Butyrospermum parkii* (shea) butter, *Shorea robusta* seed butter, murumuru butter, and any combinations thereof.

In some embodiments, the one or more cosmetically or dermatologically acceptable excipients is an antioxidant selected from: carnosine, tetrahexyldecyl ascorbate, bioflavonoids, lycopene, *Daucus carota sativa* root cell culture lysate, monoammonium glycyrrhizinate, alpha lipoic acid (thioctic acid), *Leontopodium alpinum* (edelweiss) extract, *Rosmarinus officinalis* (rosemary) leaf extract (WS), *Vitis vinifera* (grape) seed extract, *Camellia sinensis* leaf extract, *Quercus robur* wood extract, hydrolyzed olive fruit, *Olea europea* (olive) leaf extract, oleuropin, *Punica granatum* bark/fruit extract, punicalagin, ellagic acid, polyphenols, epigallocatechin (EGCG), tannins, sulforaphane, resveratrol, nordihydroguaiaretic acid, and any combinations thereof.

In some embodiments, the one or more cosmetically or dermatologically acceptable excipients is a buffer selected from: ascorbic acid, citric acid, lactic acid, glycolic acid, tartaric acid, malic acid, L-arginine, potassium hydroxide, sodium hydroxide, triethanolamine, sodium bicarbonate, and any combinations thereof.

In some embodiments, the one or more cosmetically or dermatologically acceptable excipients is a salt selected from: calcium chloride, magnesium chloride, magnesium sulfate, potassium chloride, potassium glycol sulfate, sodium chloride, and any combinations thereof.

In some embodiments, the one or more cosmetically or dermatologically acceptable excipients is an aliphatic alcohol selected from: lauric acid, palmitic acid, stearic acid, arachidic alcohol, behenyl alcohol, cetearyl alcohol, cetyl alcohol, isocetyl alcohol, isostearyl alcohol, lauryl alcohol, myristyl alcohol, stearyl alcohol, C30-50 alcohols, lanolin alcohol, and any combinations thereof.

In some embodiments, the one or more cosmetically or dermatologically acceptable excipients is a perfuming ingredient. In some embodiments, the perfuming ingredient includes a fragrance. In some embodiments, the fragrance includes limonene.

Solvents

The hair cleanser composition includes one or more solvents. In some embodiments, the one or more solvents or is selected from: water, dimethyl isosorbide, triethyl citrate, phenethyl benzoate, dicaprylyl maleate, dilinoleic acid/propanediol copolymer, lower alcohols containing from 1 to 6 carbon atoms, such as ethanol; polyols such as glycerine, glycols such as butylene glycol, isoprene glycol, propylene glycol, dipropylene glycol, propanediol, isopentyldiol, polyethylene glycols such as PEG-8, sorbitol, sugars such as glucose, fructose, maltose, lactose, sucrose; and any combinations thereof.

In some embodiments, the concentration (% w/w) of the one or more solvents in the hair cleanser composition is between about 50% to about 90%. In some embodiments, the concentration of the one or more solvents in the hair cleanser composition is about 50%, about 55%, about 60%, about 65%, 70%, about 75%, about 80%, about 85%, about 90%, and any values therebetween. In some embodiments, the concentration of the one or more solvents in the hair cleanser composition is between about 50% to about 90%, between about 55% to about 85%, between about 60% to about 80%, between about 65% to about 80%, and between about 70% to about 80%.

Formulations

In some embodiments, the hair cleanser composition comprises:

- one or more solvents;
- one or more peptides;
- one or more hair conditioners;
- one or more skin conditioners;
- one or more cleansing agents; and
- one or more cosmetically or dermatologically acceptable excipients;
- wherein the one or more peptides comprises a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO:1131, or a combination thereof.

In some embodiments, the hair cleanser composition comprises:

- between about 50% to about 90% (% w/w) of one or more solvents;
- between about 0.0001% to about 1.0% (% w/w) of one or more peptides;
- between about 0.01% to about 10.0% (% w/w) of one or more hair conditioners;
- between about 0.01% to about 5.0% (% w/w) one or more skin conditioners;
- between about 0.1% to about 20% (% w/w) one or more cleansing agents; and
- between about 0.1% to about 30% (% w/w) one or more cosmetically or dermatologically acceptable excipients;
- wherein the one or more peptides comprises a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO:1131, or a combination thereof.

In some embodiments, the hair cleanser composition comprises:

- between about 55% to about 85% (% w/w) of one or more solvents;
- between about 0.0001% to about 0.9% (% w/w) of one or more peptides;
- between about 0.20% to about 9% (% w/w) of one or more hair conditioners;
- between about 0.01% to about 0.95% (% w/w) one or more skin conditioners;
- between about 0.3% to about 18% (% w/w) one or more cleansing agents; and
- between about 0.5% to about 28.0% (% w/w) one or more cosmetically or dermatologically acceptable excipients;
- wherein the one or more peptides comprises a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO:1131, or a combination thereof.

In some embodiments, the hair cleanser composition comprises:

- between about 55% to about 85% (% w/w) of one or more solvents;

between about 0.0001% to about 0.9% (% w/w) of one or more peptides;

between about 0.20% to about 9% (% w/w) of one or more hair conditioners;

between about 0.01% to about 0.95% (% w/w) one or more skin conditioners;

between about 0.3% to about 18% (% w/w) one or more cleansing agents selected from: an anionic surfactant, an amphoteric surfactant, a non-ionic surfactant, a biosurfactant, and any combinations thereof; and between about 0.5% to about 28.0% (% w/w) one or more cosmetically or dermatologically acceptable excipients selected from: preservatives, antioxidants, thickeners, chelating agents, co-solvents, sunscreen agents, vitamins, dyes, hair coloring agents, proteins, amino acids, organic polymers, natural extracts such as plant extracts, humectants, fragrances, perfumes, oils, emollients, lubricants, butters, penetrants, thickeners, viscosity modifiers, polymers, resins, hair fixatives, silicones, film formers, surfactants, detergents, emulsifiers, opacifying agents, volatiles, propellants, liquid vehicles, carriers, salts, pH adjusting agents (buffers), neutralizing agents, buffers, hair conditioning agents, anti-static agents, anti-frizz agents, anti-dandruff agents, absorbents, and any combinations thereof;

wherein the one or more peptides comprises a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO:1131, or a combination thereof.

In some embodiments, the hair cleanser composition comprises:

between about 55% to about 85% (% w/w) of one or more solvents selected from: water, dimethyl isosorbide, triethyl citrate, phenethyl benzoate, dicaprylyl maleate, dilinoleic acid/propanediol copolymer, lower alcohols containing from 1 to 6 carbon atoms, such as ethanol; polyols such as glycerine, glycols such as butylene glycol, isoprene glycol, propylene glycol, dipropylene glycol, propanediol, isopentyldiol, polyethylene glycols such as PEG-8, sorbitol, sugars such as glucose, fructose, maltose, lactose, sucrose; and any combinations thereof;

between about 0.0001% to about 0.9% (% w/w) of one or more peptides;

between about 0.20% to about 9% (% w/w) of one or more hair conditioners selected from: panthenol, salicylic acid, sodium salicylate, carnosine, tetrahexyldecyl ascorbate, hyaluronic acid/sodium hyaluronate, hydrolyzed hyaluronic acid, sarcosine, PCA, arginine PCA, brassicyl valinate esylate, brassicyl isoleucinate esylate, brassica alcohol, glycolipids, glycosphingolipids, sphinganine, *Rubus ideaus* (raspberry) leaf extract, bis-ethyl(isostearylimidazoline) isostearamide, *Camellia sinensis* leaf extract, *Carthamus tinctorius* (safflower) seed extract, *Glycine soja* (soybean) seed extract, *Elaeis guineensis* (palm) fruit extract, *Oryza sativa* (rice) extract, hydrolyzed *Adansonia digitata* seed extract, hydrolyzed corn starch, behenyl/stearyl aminopropanediol esters, C10-40 isoalkylamidopropylethyldimonium ethosulfate, *Linum usitatissimum* (linseed) extract, *Salva hispanica* seed extract, *Astrocaryum murumuru* fruit extract, *Moringa oleifera* seed extract, cinnamidopropyltrimonium chloride, hydroxypropyl guar hydroxypropyltrimonium chloride, *Trifolium pratense* (clover) flower extract, *Opuntia ficus-indica* stem extract, *Kappaphycus alvarezii* extract, *Laminaria saccharina* extract, guar hydroxypropyltriammonium chloride, bis-diglyceryl polyacyladipate-2, hydroxypropylgluconamide, hydroxypropylammonium gluconate, biosaccharide gum-4, *Prunus amygdalus dulcic* (sweet almond) seed extract, soybean glycerides, *Butyrospermum parkii* (shea) butter unsaponifiables, hydrolyzed chestnut extract, glyceryl rosinate, sodium methoxy peg-16 maleate/styrene sulfonate copolymer, panthenyl hydroxypropyl steardimonium chloride, and any combinations thereof;

between about 0.01% to about 0.95% (% w/w) one or more skin conditioners selected from: niacinamide, allantoin, maltooligosyl glucoside, hydrogenated starch hydrolysate, *Opuntia ficus-indica* stem extract, sodium hyaluronate crosspolymer, jojoba esters, hydrolyzed jojoba esters, oleic acid, linoleic acid, linolenic acid, lactobionic acid, ursolic acid/sodium ursolate, nordihydroguaiaretic acid, ceramides, fructooligosaccharides, galactoarabinan, schizophyllan, *Anetholea anisate* leaf extract, *Tetraselmis suecica* extract, saccharide isomerase, *Alteromonas* ferment extract, *Pseudoalteromonas* ferment extract, *Corylus avellana* leaf extract, *Phyllanthus emblica* fruit extract, *Betula alba* juice, *Saccharum officinarum* (sugarcane) extract, *Rhodomyrtus tomentosa* fruit extract, *Hedychium coronarium* root extract, *Epilobium angustifolium* flower/leaf/stem extract, *Tremella fuciformis* sporocarp extract, alpha-glucan oligosaccharide, and any combinations thereof between about 0.3% to about 18% (% w/w) one or more cleansing agents selected from: an anionic surfactant, an amphoteric surfactant, a non-ionic surfactant, a biosurfactant, and any combinations thereof and between about 0.5% to about 28.0% (% w/w) one or more cosmetically or dermatologically acceptable excipients selected from: preservatives, antioxidants, thickeners, chelating agents, co-solvents, sunscreen agents, vitamins, dyes, hair coloring agents, proteins, amino acids, organic polymers, natural extracts such as plant extracts, humectants, fragrances, perfumes, oils, emollients, lubricants, butters, penetrants, thickeners, viscosity modifiers, polymers, resins, hair fixatives, silicones, film formers, surfactants, detergents, emulsifiers, opacifying agents, volatiles, propellants, liquid vehicles, carriers, salts, pH adjusting agents (buffers), neutralizing agents, buffers, hair conditioning agents, anti-static agents, anti-frizz agents, anti-dandruff agents, absorbents, and any combinations thereof;

wherein the one or more peptides comprises a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO:1131, or a combination thereof.

In some embodiments, the hair cleanser composition comprises:

between about 55% to about 85% (% w/w) of one or more solvents selected from: water, dimethyl isosorbide, triethyl citrate, phenethyl benzoate, dicaprylyl maleate, dilinoleic acid/propanediol copolymer, lower alcohols containing from 1 to 6 carbon atoms, such as ethanol; polyols such as glycerine, glycols such as butylene glycol, isoprene glycol, propylene glycol, dipropylene glycol, propanediol, isopentyldiol, polyethylene glycols such as PEG-8, sorbitol, sugars such as glucose, fructose, maltose, lactose, sucrose; and any combinations thereof between about 0.0001% to about 0.9% (% w/w) of one or more peptides;

between about 0.20% to about 9% (% w/w) of one or more hair conditioners selected from: panthenol, salicylic acid, sodium salicylate, carnosine, tetrahexyldecyl ascorbate, hyaluronic acid/sodium hyaluronate, hydrolyzed hyaluronic acid, sarcosine, PCA, arginine PCA, brassicyl valinate esylate, brassicyl isoleucinate esylate, brassica alcohol, glycolipids, glycosphingolipids, sphinganine, *Rubus ideaus* (raspberry) leaf extract, bis-ethyl(isostearylimidazoline) isostearamide, *Camellia sinensis* leaf extract, *Carthamus tinctorius* (safflower) seed extract, *Glycine soja* (soybean) seed extract, *Elaeis guineensis* (palm) fruit extract, *Oryza sativa* (rice) extract, hydrolyzed *Adansonia digitata* seed extract, hydrolyzed corn starch, behenyl/stearyl aminopropanediol esters, C10-40 isoalkylamidopropylethyldimonium ethosulfate, *Linum usitatissimum* (linseed) extract, *Salva hispanica* seed extract, *Astrocaryum murmurmuru* fruit extract, *Moringa oleifera* seed extract, cinnamidopropyltrimonium chloride, hydroxypropyl guar hydroxypropyltrimonium chloride, *Trifolium pratense* (clover) flower extract, *Opuntia ficus-indica* stem extract, *Kappaphycus alvarezii* extract, *Laminaria saccharina* extract, guar hydroxypropyltriammonium chloride, bis-diglyceryl polyacyladipate-2, hydroxypropylgluconamide, hydroxypropylammonium gluconate, biosaccharide gum-4, *Prunus amygdalus dulcic* (sweet almond) seed extract, soybean glycerides, *Butyrospermum parkii* (shea) butter unsaponifiables, hydrolyzed chestnut extract, glyceryl rosinate, sodium methoxy peg-16 maleate/styrene sulfonate copolymer, panthenyl hydroxypropyl steardimonium chloride, and any combinations thereof;

between about 0.01% to about 0.95% (% w/w) one or more skin conditioners selected from: niacinamide, allantoin, maltooligosyl glucoside, hydrogenated starch hydrolysate, *Opuntia ficus-indica* stem extract, sodium hyaluronate crosspolymer, jojoba esters, hydrolyzed jojoba esters, oleic acid, linoleic acid, linolenic acid, lactobionic acid, ursolic acid/sodium ursolate, nordihydroguaiaretic acid, ceramides, fructooligosaccharides, galactoarabinan, schizophyllan, *Anetholea anisate* leaf extract, *Tetraselmis suecica* extract, saccharide isomerase, *Alteromonas* ferment extract, *Pseudoalteromonas* ferment extract, *Corylus avellana* leaf extract, *Phyllanthus emblica* fruit extract, *Betula alba* juice, *Saccharum officinarum* (sugarcane) extract, *Rhodomyrtus tomentosa* fruit extract, *Hedychium coronarium* root extract, *Epilobium angustifolium* flower/leaf/stem extract, *Tremella fuciformis* sporocarp extract, alpha-glucan oligosaccharide, and any combinations thereof;

between about 0.3% to about 18% (% w/w) one or more cleansing agents selected from: sodium methyl 2-sulfolaurate, sodium lauryl sulfoacetate, disodium 2-sulfolaurate, alkylbenzene sulfonates, ammonium lauryl sulfate, ammonium xylenesulfonate, sodium laureth sulfate, sodium lauryl sulfate, sodium lauryl sulfoacetate, sodium 2-sulfolaurate, sodium myreth sulfate, sodium xylenesulfonate, sodium $C_{14-16}$ olefin sulfonate, sodium $C_{14-16}$ alpha olefin sulfonate, disodium lauryl sulfosuccinate, sodium methyl cocoyl taurate, sodium cocoyl isethionate, sodium lauryl isethionate, sodium cocoyl sarcosinate, sodium lauroyl sarcosinate, sodium myristoyl sarcosinate, lauroyl sarcosine, cocoyl sarcosine, myristoyl sarcosine, oleoyl sarcosine, myristoyl/stearoyl sarcosine, sodium lauroyl glutamate, sodium cocoyl glutamate, disodium cocoyl glutamate, cocoyl glutamic acid, lauroyl glutamic acid, potassium cocoyl glutamate, potassium lauroyl glutamate, potassium myristoyl glutamate, sodium myristoyl glutamate, sodium stearoyl glutamate, disodium stearoyl glutamate, sodium palmoyl glutamate, sodium lauroyl lactylate, sodium *Astrocaryum murumuruate*, sodium laurylglucosides hydroxypropylsulfonate, disodium laurylglucosides hydroxypropyl citrate, sodium hydroxypropylsulfonate laurylglucoside crosspolymer, dioctyl sodium sulfosuccinate, cocamindopropyl hydroxysultaine, cocamidopropyl betaine, coco betaine, betaine, cocoamphoacetate, cocoamphodipropionate, disodium cocoamphodiacetate, disodium cocoamphodipropionate, lauryl betaine, lauramidopropyl betaine, lauramidopropyl hydroxysultaine, lauryl hydroxysultaine, sodium dilauramidoglutamide lysine, sodium cocoamphopropionate, lauroamphoacetate, decyl glucoside, lauryl glucoside, coco-glucoside, cocoyl methyl glucamide, capryloyl/caproyl methyl glucamide, lauroyl/myristoyl methyl glucamide, cocamidopropylamine oxide, decylamine oxide, *Sapindus mukorossi* (soapnut) extract, saponin, lipopeptide, canola sophorolipid, potassium cocoyl hydrolyzed oat protein, *starmella bombicola/Brassica* oil ferment, glycoside, glycolipid, rhamnolipid, phospholipid, sophorolipid, and any combinations thereof; and between about 0.5% to about 28.0% (% w/w) one or more cosmetically or dermatologically acceptable excipients selected from: caprylic/capric/diglyceryl succinate, C14-16 glycol palmitate, C18-20 glycol isostearate, cocamidopropyl lauryl ether, dipentaerythrityl hydroxystearate, dipentaerythrityl hydroxyisostearate, dipentaerythrityl hexacaprate/caprylate, palm kernel glycerides, lecithin, hydrogenated lecithin, phosphatidylcholine, C12-16 alcohols, palmitic acid, glyceryl behenate, glyceryl stearate, glyceryl stearate citrate, glyceryl oleate citrate, sorbitan laurate, lauryl laurate, sorbitan olivate, cetearyl olivate, glyceryl stearate citrate, sodium stearoyl lactylate, sodium stearoyl glutamate, sodium cocoyl glutamate, caprylyl/capryl glucoside, polyhydroxystearic acid, phenethyl alcohol, sodium surfactin, polyglycerin-3, polyglyceryl-3 distearate, polyglyceryl-3 diisostearate, polyglyceryl-3 cocoate, polyglyceryl-3 dicitrate/stearate, polyglyceryl-3 beeswax, polyglyceryl-3 polyricinoleate, polyglyceryl-4 oleate, polyglyceryl-4 caprate, polylgylceryl-4 laurate, polyglyceryl-6 caprylate, polyglyceryl-6 stearate, polyglyceryl-6 distearate, polyglyceryl-6 behenate, polyglyceryl-6 polyhydroxystearate, polyglyceryl-6 oleate, polyglyceryl-6 ricinoleate, polyglyceryl-6 polyricinoleate, polyglyceryl-10 laurate, candelilla/jojoba/rice bran polyglyceryl-3 esters, stearoyl glutamic acid, Polysorbate-20, polyglyceryl-10 laurate, polyglyceryl-6 caprylate, polyglyceryl-3 cocoate, polyglyceryl-4 caprate, polyglyceryl-6 ricinoleate, polyglyceryl-6 caprylate, sodium surfactin, phytic acid, sodium phytate, caprylhydroxamic acid, trisodium dicarboxymethyl alaninate, gluconic acid, sodium gluconate, pentasodium pentetate, sodium carboxymethyl inulin, tetrasodium glutamate diacetate, trisodium ethylenediamine succinate, sodium thiosulfate, diiospropyl oxalate, disodium EDTA, disodium EDTA-copper, HEDTA, oxalic acid, potassium citrate, sodium citrate, dodium oxalate, TEA-EDTA, tetrasodium EDTA, trisodium EDTA, trisodium HEDTA, benzoic acid, butyl paraben, diazolidinyl urea, DMDM hydantoin, ethyl paraben, imidazolidinyl urea, iodopropynyl butylcarbamate, isobutyl paraben, methyl paraben, methylchloroisothiazolinone, methylisothiazolinone, phenoxyethanol, propyl paraben, sodium benzoate, potassium sorbate, ethylhexylglycerin, gluconolactone, lauryl lactate, hydroxypropyl starch phosphate, acrylates copolymer, ammonium acryloyldimethyltaurate, sodium acryloyldimethyltaurate/VP copolymer, sodium acrylate/sodium acryloyldimethyl taurate copolymer, sodium polyacrylate, polyacrylate crosspolymer-11, carbomer, acrylates/C10-30 alkyl acrylate crosspolymer, hydroxyethyl acrylate/sodiumacryloyldimethyltaurate copolymer, lithium magnesium sodium silicate, sodium magnesium fluorosilicate, glycol distearate, hydrogenated castor oil, hydrogenated castor oil hydroxystearate, hydrogenated castor oil isostearate, hydrogenated castor oil stearate, hydrogenated castor PEG-8 esters, quaternary ammonium compounds, behentrimonium chloride, behentrimonium methosulfate, cetrimonium chloride, cetrimonium methosulfate, benzalkonium chloride, benzethonium chloride, cinnamidopropyltrimonium chloride, cocotrimonium chloride, dicetyldimonium chloride, dicocodimonium chloride, laurtrimonium chloride, stearamidopropyl dimethylamine, steartrimonium chloride, stearalkonium chloride, tricetyldimonium chloride, PCA ethyl cocoyl arginate, C10-40 isoalkylamidopropylethyldimonium ethosulfate, dipalmitoylethyl hydroxyethylmonium methosulfate, shea butteramidopropyltrimonium chloride, xanthan gum, pullulan, algin, *tetragonoloba* (guar) gum, *sclerotium* gum, acacia Senegal gum, cellulose, cellulose gum, carboxymethylcellulose, carbomer, hydroxypropyl starch phosphate, guar hydroxypropyltrimonium chloride, carboxymethyl hydroxyethyl cellulose, carboxymethyl hydroxypropyl guar, cellulose, ethyl cellulose, hydroxybutyl methylcellulose, hydroxyethylcellulose, hydroxymethylcellulose, lauryl polyglucose, L-Cysteine, 1,2,6 hexanetriol, dipropylene glycol, glycerin, butylene glycol, caprylyl glycol, pentylene glycol, isopentyldiol, hexylene glycol, panthenol, phytantriol, propylene glycol, propanediol, sodium PCA, sorbitol, triethylene glycol, polyglyceryl sorbitol, glucose, fructose, mannitol, xylitol, inositol, trehalose, polydextrose, potassium PCA, hydrogenated honey, hyaluronic acid, inositol, erythritol, capryl glycol, acetamidoethoxyethanol, polyquaternium-10, polyquaternium-7, polyquaternium-11, polyquaternium-57, quaternium-15, quaternium-18, quaternium-22, quaternium-87, guar hydroxypropyltrimonium chloride, decyl glucoside, lauryl glucoside, coco-glucoside, cocoyl methyl glucamide, capryloyl/caproyl methyl glucamide, lauroyl/myristoyl methyl glucamide, cocamidopropylamine oxide, decylamine oxide, amodimethicone, amodimethicone, dimethicone cyclomethicone, cyclopentasiloxane, dimethicone, dimethicone copolyol, dimethiconol, hydrolyzed wheat protein hydroxypropyl polysiloxane, trimethylsilylamodimethicone, cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl silk amino acids, cocoyl hydrolyzed collagen, cocoyl hydrolyzed keratin, hydrolyzed keratin, hydrolyzed oat flour, hydrolyzed silk, hydrolyzed silk protein, hydrolyzed soy protein, hydrolyzed wheat protein, hydrolyzed quinoa, hydrolyzed elastin, hydrolyzed collagen, keratin, potassium cocoyl hydrolyzed collagen, retinol, retinyl palmitate, ascorbic acid, tocopherol, tocopherol acetate, Aloe barbadensis leaf extract, *Yucca schidigera* leaf extract, *Yucca schidigera* root extract, *Camellia sinensis* leaf extract, *Equisetum arvense* leaf extract, *Hamamelis virginiana* leaf extract, *Macrocystis pyrifera* kelp extract, isopropyl lauroyl sarcosinate, phenethyl benzoate, C12-15 alkyl benzoate, caprylic/capric triglyceride, cetyl octanoate, octyldodecanol, dilinoleic acid/propanediol copolymer, isoamyl laurate, oleic acid, isohexadecane, squalane, isopropyl palmitate, polycitronellol, diheptyl succinate, capryloyl glycerin/sebacic acid copolymer, PPG-3 benzyl ether ethylhexanoate, hydrogenated vegetable oil, triheptanoin, diisopropyl sebacate, diisopropyl adipate, propylene glycol dibenzoate, propoxytetramethyl piperidinyl dimethicone, castor oil/IPDI copolymer, butylene glycol cocoate, butylene glycol dicaprylate/dicaprate (dispersant), propylene glycol dicaprylate/dicaprate, triolein (algae oil), propylene glycol dicaprylate/dicaprate, phytosteryl/octyldodecyl lauroyl glutamate, C10-18 triglycerides, isostearyl alcohol, diisostearyl malate, isoamyl laurate, *isoamyl cocoate, hemisqualane, polycitronellol acetate, ethyl macadamiate, cococaprylate/caprate, coconut alkanes, C9-12 alkane, C13-15 alkane, C13-16 isoalkane, neopentyl glycol diheptanoate, hydrogenated ethylhexyl olivate, hydrogenated olive oil unsaponifiables, undecane, tridecane, isododecane, caprylyl caprylate/caprate, cetyl stearate, cetearyl stearate, decyl oleate, glyceryl stearate, glyceryl adipate, glyceryl arachidate, glyceryl arachidonate, glyceryl behenate, glyceryl caprate, glyceryl caprylate, glyceryl caprylate/caprate, glyceryl citrate/lactate/linoleate/oleate, glyceryl cocoate, glyceryl diarachidate, glyceryl dibehenate, glyceryl dierucate, glyceryl dihydroxystearate, glyceryl diisopalmitate, glyceryl diisostearate, glyceryl dilaurate, glyceryl dilinoleate, glyceryl dimyristate, glyceryl dioleate, glyceryl dipalmitate, glyceryl dipalmitoleate, glyceryl diricinoleate, glyceryl distearate, glyceryl erucate, glycol stearate, isocetyl stearate, isopropyl myristate, isopropyl palmitate, isopropyl stearate, isostearyl stearate, octyl palmitate, octyl stearate, propylene glycol dicaprylate/dicaprate, sorbitan benzoate, sorbitan caprylate, sorbitan isostearate, sorbitan laurate, sorbitan tristearate, stearyl stearate, tocopheryl linoleate, olive oil, avocado oil, coconut oil, sunflower oil, jojoba oil, argan oil, castor oil, almond oil, *Sesamum indicum* (sesame) seed oil, *Prunus areniaca* (apricot) kernel oil, *Crambe abyssinica* seed oil, *Oryza sativa* (rice) bran oil, *Vitis vinifera* (grape) seed oil, *Passiflora edulis* seed oil, meadowfoam seed oil, *Butyrospermum parkii* (shea) butter, *Shorea robusta* seed butter, murumuru butter, carnosine, tetrahexyldecyl ascorbate, bioflavonoids, lycopene, *Daucus carota sativa* root cell culture lysate, monoammonium glycyrrhizinate, alpha lipoic acid (thioctic acid), *Leontopodium alpinum* (edelweiss) extract, *Rosmarinus officinalis* (rosemary) leaf extract (WS), *Vitis vinifera* (grape) seed extract, *Camellia sinensis* leaf extract, *Quercus robur* wood extract, hydrolyzed olive fruit, *Olea europea* (olive)

leaf extract, oleuropin, *Punica granatum* bark/fruit extract, punicalagin, ellagic acid, polyphenols, epigallocatechin (EGCG), tannins, sulforaphane, resveratrol, nordihydroguaiaretic acid, ascorbic acid, citric acid, lactic acid, glycolic acid, tartaric acid, malic acid, L-arginine, potassium hydroxide, sodium hydroxide, triethanolamine, sodium bicarbonate, calcium chloride, magnesium chloride, magnesium sulfate, potassium chloride, potassium glycol sulfate, sodium chloride, lauric acid, palmitic acid, stearic acid, arachidic alcohol, behenyl alcohol, cetearyl alcohol, cetyl alcohol, isocetyl alcohol, isostearyl alcohol, lauryl alcohol, myristyl alcohol, stearyl alcohol, C30-50 alcohols, lanolin alcohol, and any combination thereof;

wherein the one or more peptides comprises a peptide sequence comprising SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO:1131, or a combination thereof.

EXAMPLES

The following examples are included for illustrative purposes only and are not intended to limit the scope of the invention.

Example 1. Preparation of Hair Cleanser

An exemplary hair cleanser composition is provided in Tables 2-6. The exemplary hair cleanser compositions are made by conventional formulation and mixing techniques or by mixing together one or more polyols (e.g. glycerin), water and surfactants along with any solids that need to be melted at an elevated temperature. The ingredients are mixed thoroughly at the elevated temperature and then cooled to ambient temperature. Additional ingredients are added to the cooled product. The amount stated reflects the weight percent of the active material, unless otherwise specified.

TABLE 2

Exemplary hair cleanser composition

| Ingredient | Function | Percent formula (% w/w) |
|---|---|---|
| Water (Aqua) (Eau) | Solvent | 80.8124 |
| Sodium $C_{14-16}$ Olefin Sulfonate | Surfactant | 10.99 |
| Cocamidopropyl Betaine | Surfactant | 4.33 |
| Sodium Methyl 2-Sulfolaurate | Surfactant | 0.85 |
| Sodium Lauryl Sulfoacetate | Surfactant | 1 |
| Caprylyl Glycol | Skin Conditioning | 0.255 |
| Citric Acid | Buffering | 0.25 |
| Sodium Phytate | Chelating | 0.23 |
| Panthenol | Hair Conditioning | 0.22 |
| Guar Hydroxypropyltrimonium Chloride | Skin Conditioning | 0.18 |
| Disodium 2-Sulfolaurate | Surfactant | 0.16 |
| Glycerin | Humectant | 0.16 |
| Caprylhydroxamic Acid | Chelating | 0.10 |
| Benzoic Acid | Preservative | 0.06 |
| SEQ ID 412 | Peptide | 0.00012 |
| Fragrance (Parfum) | Perfuming | 0.298763 |
| Limonene | Perfuming | 0.103717 |

TABLE 3

Exemplary hair cleanser composition

| Ingredient | Function | Percent formula (% w/w) |
|---|---|---|
| Water (Aqua) (Eau) | Solvent | 81.9849 |
| Sodium $C_{14-16}$ Olefin Sulfonate | Surfactant | 9.75 |
| Cocamidopropyl Betaine | Surfactant | 3.84 |
| Sodium Methyl 2-Sulfolaurate | Surfactant | 1.0 |
| Sodium Lauryl Sulfoacetate | Surfactant | 1.00 |
| Caprylyl Glycol | Skin Conditioning | 0.75 |
| Citric Acid | Buffering | 0.235 |
| Sodium Phytate | Chelating | 0.2 |
| Panthenol | Hair Conditioning | 0.20 |
| Guar Hydroxypropyltrimonium Chloride | Skin Conditioning | 0.20 |
| Disodium 2-Sulfolaurate | Surfactant | 0.15 |
| Glycerin | Humectant | 0.15 |
| Caprylhydroxamic Acid | Chelating | 0.10 |
| Benzoic Acid | Preservative | 0.04 |
| SEQ ID 400 | Peptide | 0.0001 |
| Fragrance (Parfum) | Perfuming | 0.310316 |
| Limonene | Perfuming | 0.089684 |

TABLE 4

Exemplary hair cleanser composition

| Ingredient | Function | Percent formula (% w/w) |
|---|---|---|
| Water (Aqua) (Eau) | Solvent | 83.9999 |
| Sodium $C_{14-16}$ Olefin Sulfonate | Surfactant | 9.31 |
| Cocamidopropyl Hydroxysultaine | Surfactant | 2.89 |
| Sodium Methyl 2-Sulfolaurate | Surfactant | 0.9 |
| Canola Sophorolipids | Surfactant | 0.95 |
| Caprylyl Glycol | Skin Conditioning | 0.65 |
| Glycolic Acid | Buffering | 0.144 |
| Sodium Phytate | Chelating | 0.1 |
| Sarcosine | Hair Conditioning | 0.21 |
| Guar Hydroxypropyltrimonium Chloride | Skin Conditioning | 0.19 |
| Disodium 2-Sulfolaurate | Surfactant | 0.025 |
| Glycerin | Humectant | 0.023 |
| Caprylhydroxamic Acid | Chelating | 0.11 |
| Benzoic Acid | Preservative | 0.03 |
| SEQ ID 409 | Peptide | 0.00015 |
| Fragrance (Parfum) | Perfuming | 0.367854 |
| Limonene | Perfuming | 0.099765 |

TABLE 5

Exemplary hair cleanser composition

| Ingredient | Function | Percent formula (% w/w) |
|---|---|---|
| Water (Aqua) (Eau) | Solvent | 85.2134 |
| Sodium $C_{14-16}$ Olefin Sulfonate | Surfactant | 9.02 |
| Cocamidopropyl Hydroxysultaine | Surfactant | 1.89 |
| Sodium Methyl 2-Sulfolaurate | Surfactant | 0.8 |
| Canola Sophorolipids | Surfactant | 0.9 |
| Caprylyl Glycol | Skin Conditioning | 0.55 |
| Glycolic Acid | Buffering | 0.16 |
| Sodium Phytate | Chelating | 0.1 |
| Sarcosine | Hair Conditioning | 0.21 |
| Guar Hydroxypropyltrimonium Chloride | Skin Conditioning | 0.19 |
| Disodium 2-Sulfolaurate | Surfactant | 0.025 |
| Glycerin | Humectant | 0.15 |
| Caprylhydroxamic Acid | Chelating | 0.10 |
| Benzoic Acid | Preservative | 0.04 |
| SEQ ID 432 | Peptide | 0.0001 |

TABLE 5-continued

| Exemplary hair cleanser composition | | |
|---|---|---|
| Ingredient | Function | Percent formula (% w/w) |
| Fragrance (Parfum) | Perfuming | 0.31466 |
| Limonene | Perfuming | 0.089684 |

TABLE 6

| Exemplary hair cleanser composition | | |
|---|---|---|
| Ingredient | Function | Percent formula (% w/w) |
| Water (Aqua) (Eau) | Solvent | 80.2333 |
| Sodium $C_{14-16}$ Olefin Sulfonate | Surfactant | 10.75 |
| Cocamidopropyl Betaine | Surfactant | 4.5 |
| Sodium Methyl 2-Sulfolaurate | Surfactant | 0.75 |
| Sodium Lauryl Sulfoacetate | Surfactant | 1 |
| Caprylyl Glycol | Skin Conditioning | 0.82674 |
| Citric Acid | Buffering | 0.25 |
| Sodium Phytate | Chelating | 0.333 |
| Panthenol | Hair Conditioning | 0.22 |
| Guar Hydroxypropyltrimonium Chloride | Skin Conditioning | 0.16 |
| Disodium 2-Sulfolaurate | Surfactant | 0.18 |
| Glycerin | Humectant | 0.19 |
| Caprylhydroxamic Acid | Chelating | 0.09 |
| Benzoic Acid | Preservative | 0.06 |
| SEQ ID 401 | Peptide | 0.00013 |
| Fragrance (Parfum) | Perfuming | 0.335674 |
| Limonene | Perfuming | 0.121156 |

Example 2. Evaluations of Hair Cleanser Efficacy During and after Cleansing

A hair cleanser composition is prepared according to Example 1. The hair cleanser composition is evaluated using a survey to determine the sensory effect of the hair cleanser on the glossiness, texture (i.e., slipperiness), elasticity and stiffness. The sensory effect is evaluated during washing and after drying.

A human hair bundle having a length of 25 cm, a width of 5.5 cm, and a weight of 10 g is lightly rinsed with warm water at 40° C. Excess water is removed, and the hair bundle is foamed thoroughly for about 1 minute using 1.5 g of the hair cleanser composition per 10-gram tress of hair cleanser. A sensory evaluation is performed on the foamed hair to determine its slipperiness. The evaluation is performed by 20 people, and the total value of the evaluation is shown. Evaluation criteria are 4: glide well, 3: slightly slip, 2: does not slip very well, and 1: do not slip.

A human hair bundle having a length of 25 cm, a width of 5.5 cm, and a weight of 10 g is lightly rinsed with warm water at 40° C. Excess water is removed, and the hair bundle is foamed thoroughly for about 1 minute using 1.5 g of the hair cleanser composition per 10-gram tress of hair cleanser. The foamed hair is rinsed with running water (2 L/min) at 40° C. for 1 minute. Excess moisture is removed using a towel and hair bundle is air-dried. After drying, a sensory evaluation is performed on the dried hair to determine its glossiness and unity. The evaluation is performed by 20 people, and the total value of the evaluation is shown. Evaluation criteria are 4: good, 3: slightly good, 2: not very good, and 1: not good.

A human hair bundle having a length of 25 cm, a width of 5.5 cm, and a weight of 10 g is thoroughly rinsed with warm water at 40° C. The hair bundle is foamed thoroughly for about 1 minute using 5 g or 10 g of the hair cleanser composition. The foamed hair is rinsed thoroughly with running water (2 L/min) at 40° C. Excess moisture is removed using a towel and hair bundle is dried with warm air from a hair dryer. After drying, a sensory evaluation is performed on the dried hair to determine its elasticity. The evaluation is performed by 25 people, and the total value of the evaluation is shown. Evaluation criteria are 4: significant improvement in elasticity, 3: improvement of elasticity and stiffness is seen, 2: a slight improvement in elasticity, 1: no improvement of elasticity, and 0: lost elasticity.

Example 3. Evaluation of Cleanser Efficacy Using FTIR

Bleached hair samples may be obtained. Some of the bleached hair samples may be treated with the hair cleanser compositions described herein. For both the treated and untreated samples cross-sections will be prepared using a cryostat and the cross sections will be examined using Attenuated Total Reflection Fourier Transform Infrared Spectroscopy (ATR-FTIR). Using this technique hyperspectral images with be produced which may be used to visualize the lipid content inside the hair fiber, assess hair damage inside the hair fibers (i.e., chemical treatment, or UV exposure), identify hair structure modifications (i.e., protein conformation, or lipid organization), evaluate hair hydration (i.e., water content), visualize active penetration inside the hair fiber, and determine the efficacy of the cleanser for clearing sebum and products from the hair strand.

Single fibers of both the treated and untreated samples may scanned longitudinally using ATR-FTIR, which may provide infrared images of roughly the outer 1-2 microns of the fiber surface. These hyperspectral images may be used to determine the lipid content in the cuticle, investigate the hair damage along the fiber (i.e., chemical treatment, or UV exposure), analyze the deposition of an active ingredient along the hair fiber, identify hair structure modifications (i.e., protein conformation, or lipid organization), evaluate hair hydration (i.e., water content), and determine the efficacy of the cleanser for clearing sebum and products from the hair strands.

Example 4: Evaluation of Metal Reduction/Chelation

Bleached hair samples may be obtained. Some of the bleached hair samples may be treated with the hair cleanser compositions described herein. Both the treated and untreated samples may be rinsed with hard water and examined using Time-Of-Flight Secondary Ion Mass Spectroscopy (TOF-SIMS). Spectra may be obtained for calcium, magnesium, copper, aluminum, iron, chromium, zinc, nickel, cadmium, lead, and mercury.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A hair cleanser, comprising:

(i) one or more hair conditioners comprising panthenol, *Rubus idaeus* (raspberry) leaf extract, *Carthamus tinctorius* (safflower) seed extract, hydroxypropylgluconamide, hydroxypropylammonium gluconate, hydrolyzed hyaluronic acid, or sodium hyaluronate, or a combination of two or more thereof;

(ii) sodium $C_{14-16}$ olefin sulfonate, cocamidopropyl betaine, sodium lauryl sulfoacetate, disodium 2-sulfolaurate, and sodium methyl-2-sulfolaurate, wherein the sodium $C_{14-16}$ olefin sulfonate is present at a concentration (% w/w) of about 7.0%, about 7.5%, about 8.0%, about 8.5%, about 9.0%, about 9.5% about 10.0%, or about 11.0% of a total weight of the hair cleanser, wherein the cocamidopropyl betaine is present at a concentration (% w/w) of about 2.5%, about 3.0%, about 3.5%, about 4.0%, about 4.5%, about 5.0%, or about 5.5% of a total weight of the hair cleanser.

2. The hair cleanser of claim 1, further comprising a non-ionic surfactant, a biosurfactant, or a non-ionic surfactant and a biosurfactant.

3. The hair cleanser of claim 1, further comprising a humectant.

4. The hair cleanser of claim 3, wherein the humectant is glycerin, propylene glycol, propanediol, or isopentyldiol.

5. The hair cleanser of claim 1, further comprising a buffer comprising citric acid, lactic acid, glycolic acid, malic acid, tartaric acid, L-arginine, sodium hydroxide, or potassium hydroxide, or a combination of two or more thereof.

6. The hair cleanser of claim 1, further comprising a preservative comprising phenoxyethanol, caprylhydroxamic acid, potassium sorbate, ethylhexylglycerin, gluconolactone, sodium benzoate, or benzoic acid, or a combination of two or more thereof.

7. The hair cleanser of claim 1, wherein the one or more hair conditioners in the hair cleanser is present at a concentration (% w/w) of about 0.01% to about 10%.

8. The hair cleanser of claim 1, wherein the hair cleanser has a pH of about 4 to about 6.

9. The hair cleanser of claim 1, wherein the sodium lauryl sulfoacetate, disodium 2-sulfolaurate, and sodium methyl-2-sulfolaurate are each individually present at a concentration of about 0.1% to about 10% of a total weight of the cleanser.

10. The hair cleanser of claim 9, wherein the hair cleanser has a pH of about 4 to about 6.

11. The hair cleanser of claim 1, wherein the panthenol is present at a concentration (% w/w) of about 0.01%, about 0.05%, about 0.10%, about 0.15%, about 0.20%, about 0.25%, about 0.30%, about 0.35%, about 0.40%, about 0.45%, about 0.50%, about 0.55%, about 0.60%, about 0.65%, or about 0.7%.

12. The hair cleanser of claim 1, wherein the disodium 2-sulfolaurate is present at a concentration (% w/w) of about 0.1%, about 0.2%, about 0.3%, or about 0.4%.

13. A method for cleansing hair comprising applying to the hair the hair cleanser of claim 1.

14. The hair cleanser of claim 1, wherein the hair cleanser further comprises one or more peptides comprising a peptide sequence selected from any one of SEQ ID NO: 75, SEQ ID NO: 400, SEQ ID NO: 401, SEQ ID NO: 402, SEQ ID NO: 409, SEQ ID NO: 412, SEQ ID NO: 432, SEQ ID NO: 951, and SEQ ID NO: 1131.

* * * * *